(12) United States Patent
Qasem

(10) Patent No.: US 10,835,132 B2
(45) Date of Patent: Nov. 17, 2020

(54) CENTRAL AORTIC BLOOD PRESSURE AND WAVEFORM CALIBRATION METHOD

(71) Applicant: AtCor Medical Pty Ltd, West Ryde (AU)

(72) Inventor: Ahmad Qasem, Guildford (AU)

(73) Assignee: AtCor Medical Pty Ltd, West Ryde (AU)

( * ) Notice: Subject to any disclaimer, the term of this patent is extended or adjusted under 35 U.S.C. 154(b) by 454 days.

(21) Appl. No.: 15/923,092

(22) Filed: Mar. 16, 2018

(65) Prior Publication Data

US 2018/0263513 A1    Sep. 20, 2018

Related U.S. Application Data

(60) Provisional application No. 62/472,761, filed on Mar. 17, 2017.

(51) Int. Cl.
*A61B 5/021*      (2006.01)
*A61B 5/00*       (2006.01)
(Continued)

(52) U.S. Cl.
CPC ........ *A61B 5/02108* (2013.01); *A61B 5/7235* (2013.01); *A61B 5/7278* (2013.01);
(Continued)

(58) Field of Classification Search
CPC . A61B 5/02108; A61B 5/7235; A61B 5/7278; A61B 5/02225; A61B 5/02416;
(Continued)

(56) References Cited

U.S. PATENT DOCUMENTS

| 4,796,184 A | 1/1989 | Bahr |
| 5,265,011 A | 11/1993 | O'Rourke |

(Continued)

FOREIGN PATENT DOCUMENTS

| EP | 1179318 | 2/2002 |
| EP | 1380254 | 1/2004 |

(Continued)

OTHER PUBLICATIONS

Hahn, et al., A New Approach to Reconstruction of Central Aortic Blood Pressure using "Adaptive" Transfer Function; Engineering in Medicine and Biology Society, 2008, EMBS 2008, 30th Annual International Conference of the IEEE; IEEE, 208, pp. 183-816.

(Continued)

*Primary Examiner* — Eric J Messersmith
(74) *Attorney, Agent, or Firm* — Andrus Intellectual Property Law

(57) ABSTRACT

Central systolic and diastolic pressures are measured non-invasively using a peripheral sensor to capture a patient's peripheral pulse waveform. Either the peripheral pulse waveform or a central pressure waveform generated, e.g., using a transfer method is recalibrated to account for differences between non-invasively measured systolic and diastolic pressure and invasively measured systolic and diastolic pressure. The recalibration is based, at least in part, on cardiovascular features of the patient's waveform. The determined central systolic and diastolic pressure values can be used to generate a corrected central pressure waveform having cardiovascular features preserved and maximum and minimum values set to the determined values.

44 Claims, 15 Drawing Sheets

(51) Int. Cl.

| | | |
|---|---|---|
| G16H 50/30 | (2018.01) | |
| G16H 40/63 | (2018.01) | |
| G16H 50/20 | (2018.01) | |
| A61B 5/022 | (2006.01) | |
| A61B 5/024 | (2006.01) | |

(52) U.S. Cl.
CPC ....... *A61B 5/02225* (2013.01); *A61B 5/02416* (2013.01); *A61B 2560/0228* (2013.01); *G16H 40/63* (2018.01); *G16H 50/20* (2018.01); *G16H 50/30* (2018.01)

(58) Field of Classification Search
CPC ........... A61B 2560/0228; G16H 50/30; G16H 50/20; G16H 40/63
See application file for complete search history.

(56) References Cited

U.S. PATENT DOCUMENTS

| | | | |
|---|---|---|---|
| 5,882,311 | A | 3/1999 | O'Rourke |
| 6,485,431 | B1 | 11/2002 | Campbell |
| 6,647,287 | B1 | 11/2003 | Peel et al. |
| 6,740,045 | B2 * | 5/2004 | Amano ................. A61B 5/021 600/300 |
| 6,994,675 | B2 | 2/2006 | Sharrock |
| 7,727,157 | B2 | 6/2010 | Sharrock |
| 8,100,835 | B2 | 1/2012 | Baruch |
| 8,821,403 | B2 | 9/2014 | Sharrock |
| 8,882,311 | B2 * | 11/2014 | Snell ........ F21S 8/026 362/374 |
| 9,289,138 | B2 | 3/2016 | Chowienczyk et al. |
| 9,314,170 | B2 | 4/2016 | Qasem |
| 2002/0156382 | A1 | 10/2002 | Freund et al. |
| 2002/0177781 | A1 | 11/2002 | Amano |
| 2003/0220584 | A1 | 11/2003 | Honeyager et al. |
| 2004/0024324 | A1 | 2/2004 | Bratteli |
| 2004/0059231 | A1 | 3/2004 | Narimatso et al. |
| 2004/0158162 | A1 | 8/2004 | Narimatsu |
| 2008/0287793 | A1 | 11/2008 | Hoffman |
| 2009/0131804 | A1 * | 5/2009 | Mukkamala ....... A61B 5/02108 600/485 |
| 2009/0149763 | A1 | 6/2009 | Chen et al. |
| 2009/0287097 | A1 | 11/2009 | Lowe |
| 2010/0241013 | A1 | 9/2010 | Hatib |
| 2011/0137183 | A1 * | 6/2011 | Stok ........ A61B 5/029 600/485 |
| 2011/0237961 | A1 | 9/2011 | Voss et al. |
| 2011/0270098 | A1 | 11/2011 | Chowienczyk |
| 2011/0275944 | A1 * | 11/2011 | Qasem ................. A61B 5/7225 600/493 |
| 2012/0289840 | A1 * | 11/2012 | Chen ................. A61B 5/02116 600/486 |
| 2013/0345576 | A1 * | 12/2013 | Chen ................. A61B 5/02225 600/490 |
| 2014/0316288 | A1 * | 10/2014 | Chowienczyk ........ A61B 5/725 600/485 |
| 2015/0320364 | A1 * | 11/2015 | Knoll .................. A61B 5/7264 600/494 |
| 2015/0327786 | A1 | 11/2015 | Lading |
| 2017/0196517 | A1 * | 7/2017 | Zhang .................... A61B 5/023 |
| 2018/0153415 | A1 * | 6/2018 | Lee ........................ A61B 5/746 |
| 2019/0298191 | A1 * | 10/2019 | Mukkamala ....... A61B 5/02225 |

FOREIGN PATENT DOCUMENTS

| | | |
|---|---|---|
| EP | 2070472 | 6/2009 |
| WO | 2007053868 | 5/2007 |
| WO | 2009139646 | 11/2009 |
| WO | 2010002250 | 1/2010 |
| WO | 2010058169 | 5/2010 |
| WO | 2011135446 | 11/2011 |

OTHER PUBLICATIONS

Shih, et al.., Is Noninvasive Brachial Systolic Blood Pressure an Accurate Estimate of Central Aortic Systolic Blood Pressure?; American Journal of Hypertension, vol. 29, No. 11 (2015); pp. 1283-1291.

International Search Report and Written Opinion dated Jun. 12, 2018 in co-pending PCT Application PCT/IB2018/051770.

Roman, et al., High Central Pulse Pressure is Independently Associated with Adverse Cardiovascular Outcome, Journal of American College of Cardiology, vol. 54, No. 18, Oct. 27, 2009, pp. 1730-1734.

McEniery, et al., Central Pressure Variability and Impact of Cardiovascular Risk Factors, The Anglo-Cardiff Collaborative Trial II, Hypertension, Jun. 2008, pp. 1476-1482.

Williams, et al., Differential Impact of Blood Pressure-Lowering Drugs on Central Aortic Pressure and Clinical Outcomes, Principal Results of the Conduit Artery Function Evaluation (CAFE) Study, Circulation Mar. 7, 2006, pp. 1213-1225.

Pauca, et al., Prospective Evaluation of a Method of Estimating Ascending Aortic Pressure from the Radial Artery Pressure Waveform, Hypertension, Oct. 2001, vol. 38, pp. 932-937.

Sharman, et al., Validation of a Generalized Transfer Function to Noninvasively Derive Central Blood Pressure During Exercise, Hypertension, Jun. 2006, vol. 47, pp. 1203-1208.

Wassertheurer, et al., A new oscillometric method for pulse wave analysis: comparison with a common tonometric method, Journal of Human Hypertension 24, 2010, pp. 498-504, published online Mar. 18, 1010.

Jilek, et al., Amplitude envelope slopes of oscillometric blood pressure waveforms as defined by amplitude ratios, Applied Electronics, 2009, pp. 137-140.

Mersich, et al., Identification of the cuff transfer function increases indirect blood pressure measurement accuracy, Physiological Measurement, Institute of Physics Publishing, Bristol, GB, vol. 30, No. 3, Mar. 1, 2009, pp. 323-333.

American National Standard, ANSI/AAMI/ISO 8160-2:2009, Noninvasive sphygmomanometers—Part 2: Clinical validation of automated measurement type, Section 5.2.4.1.2 Part a—Criterion 1, p. 20.

Sharman, et al., Validation of non-invasive central blood pressure devices: Artery Society task force consensus statement on protocol standardization; European Heart Journal (2017) 0, 1-10.

Cloud, et al., Estimation of central aortic pressure by SphygmoCor requires intra-arterial peripheral pressures, Clinical Science (2003) 105, 219-225.

Shoji, et al., Invasive validation of a novel brachial cuff-based oscillmetric device (SphygmoCor XCEL) for measuring central blood pressure, Journal of Hypertension 2016, 1-7.

Nichols, et al., McDonald's Blood Flow in Arteries: Theoretical, Experimental and Clinical Principles, Fifth Edition, 2005.

Roman, et al., Central Pressure More Strongly Relates to Vascular Disease and Outcome than Does Brachial Pressure, The Strong Heart Study, Hypertension 2007, 50:197-203.

Mase, et al., Feasibility of cuff-free measurement of systolic and diastolic arterial blood pressure, Journal of Electrocardiology 44 (2011) pp. 201-207.

Chen, et al., Continuous and Noninvasive Measurement of Systolic and Diastolic Blood Pressure by One Mathematical Model with the Same Model Parameters and Two Separate pulse Wave Velocities, Annals of Biomedical Engineering, vol. 40, No. 4, Apr. 2012, pp. 871-882.

Zheng, et al., Wearable Cuff-less PTT-based System for Overnight Blood Pressure Monitoring, 35th Annual International Conference of the IEEE EMBS, Osaka, Japan, Jul. 3-7, 2013, pp. 6013-6106.

Chobanian, et al., Seventh Report of the Joint National Committee on Prevention, Detection, Evaluation, and Treatment of High Blood Pressure, Hypertension, Dec. 2003, 42, pp. 1206-1252.

Mancia, et al., 2007 Guidelines for the management of arterial hypertension, European Heart Journal, 2007, 28, pp. 1462-1536.

* cited by examiner

CENTRAL AORTIC BLOOD PRESSURE AND WAVEFORM CALIBRATION METHOD

FIELD OF THE INVENTION

The invention pertains to the use of a brachial cuff device to calibrate a patient's central aortic pressure waveform. In particular, the invention relates to recalibrating the amplitude of a detected peripheral pulse waveform or the estimated central aortic pressure waveform so that the maximum and minimum values of the estimated central aortic waveform closely match the patient's invasively measured central aortic systolic and diastolic pressures.

BACKGROUND OF THE INVENTION

Arterial blood pressure is a clinically important indicator of the status of the cardiovascular system, reflective of arterial and cardiac load and an early independent predictive marker of cardiovascular events and diseases. However, to measure the inter-arterial blood pressure accurately requires an invasive procedure to insert a catheter with a pressure sensor inside the artery. As a result, non-invasive methods were created to estimate pressure at the peripheral brachial artery.

One of the earliest non-invasive methods to estimate pressure in the brachial artery is the auscultatory method which requires inflating a cuff wrapped around the patient's upper arm and brachial artery until the brachial artery occludes (i.e., no blood flow). Then, the cuff is gradually deflated and blood starts flowing with "thumping" sounds that can be detected through a stethoscope. The first "thumping" sound should occur when the cuff pressure equals the patient's systolic pressure (maximum pressure during cardiac ejection) and the last "thumping" sound should occur when the cuff pressure equals the patient's diastolic pressure (minimum pressure during cardiac filling).

For decades, the auscultatory method was used for clinical hypertension diagnosis and had become the standard for non-invasive blood pressure measurement. However, the accuracy of the measured pressure value was dependent on the operator's acute detection of the heart sound and also dependent on the rate that the operator deflated the cuff. Because the accuracy of the auscultatory method is operator dependent, an automated method was established based on detecting oscillatory pulsations measured by the brachial cuff during cuff inflation or deflation. The height of the pulse oscillation increases when the cuff pressure decreases from systolic pressure to below systolic pressure and the height of the oscillation decreases when the cuff pressure decreases from above diastolic pressure to diastolic pressure and below. Based on this concept, current "oscillometric" devices apply different algorithms to detect oscillation heights related to systolic and diastolic pressure.

Oscillometric cuff devices are often called a non-invasive blood pressure devices or NIBP devices in the art. To be accepted for clinical use, an NIBP device has to show equivalence to the standard auscultatory method based on the American National Standard for Non-Invasive Automated Blood Pressure Devices, see, ANSI/AAMI/ISO 81060-2:2009, "Non-invasive sphygmomanometers—Part 2: Clinical validation of automated measurement type," Section 5.2.4.1.2 Part a—Criterion 1, page 20 (which states that the mean error for determination of all subjects in the test "shall not be greater than 5.0 mmHg with a standard deviation no greater than 8 mmHg.") Accordingly, any oscillometric cuff device can pass the validation requirements if the average difference with the auscultatory method for systolic and diastolic pressure is not more than 5 mmHg and the standard deviation is not more than 8 mmHg. This means that approved oscillometric devices can register a difference with the standard auscultatory method reaching above 20 mmHg for some data points.

Oscillometric automated blood pressure devices have been standard in clinical practice for many years, and have also been used in medical research to assess cardiovascular risk. Even though non-invasive blood pressure (NIBP) measurement identifies a percentage of the general population at risk of cardiovascular diseases, a large group is not identified by NIBP measurement to be at risk even though they may be at risk. The main reason is that measured blood pressure varies among different NIBP devices due to the different devices having different propriety algorithms for detecting systolic and diastolic pressure. Furthermore, when compared to invasive pressure values, NIBP devices have been shown to underestimate systolic pressure and overestimate diastolic pressure, see Sharman et al., "Validation of non-invasive central blood pressure devices: Artery Society task force consensus statement on protocol standardization", *European Journal of Hypertension* 2017; Cloud et al., "Estimation of central aortic pressure by SphygmoCor® requires intra-arterial peripheral", *Clinical Science* (2003) 105, 219-225; Shoji et al., "Invasive validation of a novel brachial cuff-based oscillometric device (SphygmoCorX-CEL) for measuring central blood pressure", *Journal of Hypertension* 2016, 34. Accordingly, since measuring brachial pressure invasively is the gold standard, non-invasive measurements that closer estimate the invasive pressure and overcome the errors inherent in cuff NIBP devices would be a significant improvement in the field of blood pressure measurement and its clinical importance.

As a result, there have been attempts to determine other non-invasive blood pressure measurements that overcome the shortcomings of the NIBP devices in terms of accuracy as a marker for the cardiovascular system status and risk. One solution recognizes that brachial arterial pressure is not the same as the central aortic pressure at the heart. Based on fluid dynamic principles and hemodynamic invasive studies, blood pressure values differ at different arterial locations and the shape of the pressure pulse waveform differs significantly between the central aortic artery and peripheral (e.g. brachial, radial) arteries. Since central pressure is different than the measured brachial blood pressure and the central waveform reflects cardiac load and the functioning of the arterial system, measuring the central pressure waveform provides a more accurate marker of the status of the cardiovascular system and is a better diagnostic tool to identify cardiovascular risk.

The most widely used method to estimate central pressure non-invasively is the transfer function method, Michael O'Rourke, "Method for ascertaining the pressure pulse and related parameters in the ascending aorta from the contour of the pressure pulse in the peripheral arteries", U.S. Pat. No. 5,265,011, 1993; and Ahmad Qasem, "Brachial Cuff" U.S. Pat. No. 9,314,170, Apr. 19, 2016, both incorporated herein by reference. One or more the transfer functions, which represent the harmonics ratio between peripheral and central pressure waveforms, are calculated from invasive pressure recordings at the peripheral and central locations respectively and the mathematical characteristics represent an upper arterial model that can be applied to the general adult population. In general, the transfer function used in Applicant's SphygmoCor® systems shows that there is an amplification of the pressure as it travels from the aortic central artery to peripheral arteries and that the amplification is dependent on the waveform harmonics. To implement the transfer function central pressure method, it is desirable to measure a peripheral pulse waveform non-invasively but the waveform needs to be measured with high enough fidelity to preserve the cardiovascular features of the waveform, such as with a tonometer to measure a radial pressure waveform (O'Rourke, U.S. Pat. No. 5,265,011) or with a brachial cuff to measure a brachial volume displacement waveform (Qasem, U.S. Pat. No. 9,314,170). Then the next step in this method is to calibrate the peripheral waveform with either non-invasively measured systolic and diastolic pressure or a calculated mean pressure and the diastolic pressure. Finally, the calibrated peripheral waveform is processed by the one or more transfer functions to produce a calibrated central pressure waveform with sufficient fidelity to characteristically preserve the patient's cardiovascular features.

The transfer function central pressure method was validated by comparing the estimated central pressure waveform with invasively measured central pressure values. However, in the invasive validation, the peripheral pressure was calibrated with invasively measured peripheral SP and DP measurements thus overcoming the error in the difference between invasive and non-invasive peripheral pressure. Given that invasive peripheral systolic and diastolic pressure are not usually measured in clinical settings, the transfer function central pressure method uses NIBP measured systolic and diastolic pressure values for calibration of the non-invasively measured peripheral pulse waveform. Accordingly, the amplitude of the estimated central pressure waveform will be relative to the NIBP values, which as described above introduces error. After the TF central pressure method was introduced many clinical studies showed that it identified more subjects under cardiovascular risk than were not identified by the conventional NIBP measurement (Roman et al, "Central Pressure More Strongly Relates to Vascular Disease and Outcome than Does Brachial Pressure: The Strong Heart Study", *Hypertension.* 2007; 50:197-203). However, eliminating (or reducing) the difference between NIBP measurement and invasive pressure measurement would further improve the clinical value of central blood pressure and central blood pressure waveform analysis. Invasive pressure data has shown that differences between invasive and non-invasive brachial blood pressure and central blood pressure can be beyond 15 mmHg on 40% to 50% of the study population (Cloud et al., "Estimation of central aortic pressure by SphygmoCor® requires intra-arterial peripheral", *Clinical Science* (2003) 105, 219-225; Shoji et al., "Invasive validation of a novel brachial cuff-based oscillometric device (SphygmoCorXCEL) for measuring central blood pressure", *Journal of Hypertension* 2016, 34) Accordingly, being able to overcome the errors inherent in cuff NIBP devices would be a significant improvement for central blood pressure waveform analysis and its clinical importance.

SUMMARY OF THE INVENTION

The general purposes of the invention are: 1) to calibrate non-invasively measured central aortic pressure waveforms; and 2) to non-invasively measure central systolic and diastolic pressure, such that in both cases the non-invasive measurements more accurately estimate invasively measured equivalents. Consequently, use of the invention should render central pressure waveform analysis and non-invasive measurement of central pressure systolic and diastolic pressure more clinically helpful.

The invention applies linear and/or non-linear methods to recalibrate one of a non-invasively measured peripheral pulse waveform or an estimated central aortic pressure waveform. The recalibration is based on waveform cardiovascular features. More specifically, the invention estimates brachial systolic and diastolic pressure values using a non-invasive cuff to measure non-invasive systolic and diastolic pressure. The patient's peripheral pulse waveform is also measured, with the brachial cuff, tonometer or other non-invasive sensor such as a photodiode, and with sufficient fidelity brachial to preserve the cardiovascular features of the waveform. If the patient's brachial cuff volumetric displacement waveform is used, the brachial cuff is inflated to a constant pressure around the patient's upper arm. The brachial cuff is maintained at the constant pressure and the analog signal from the pressure sensor is recorded as the patient's brachial cuff volumetric waveform. The analog signal or its digital counterpart must be filtered through an appropriate band-pass filter, a combination of a low pass and high pass filter or another appropriate filter in order to produce a brachial cuff volumetric displacement waveform in which the cardiovascular features of the patient's waveform are preserved. Such a waveform is shown for example in FIG. 11. Importantly, the brachial cuff volumetric displacement waveform should have at least an identifiable first systolic peak, second systolic peak and incisura indicating the end of the cardiac ejection cycle. The specific filtering necessary for preserving the waveform features is dependent on the brachial cuff type and model. Since a tonometer and/or photodiode sensor are designed to measure pressure or pressure related waveforms, raw waveforms captured using these sensors should preserve the cardiovascular features without further filtering. In the next step of the method, the peripheral waveform is initially calibrated using the non-invasively cuff measured brachial systolic pressure $SP_B$ and the non-invasively cuff measured brachial diastolic pressure $DP_B$. In one embodiment of the invention, the NIBP-calibrated peripheral waveform is then converted to an estimated central aortic waveform, e.g., using the transfer function method. Based on one or more cardiovascular features of the NIBP-calibrated central pressure waveform, the estimated central aortic waveform is then recalibrated such that the maximum and the minimum correspond accurately to the invasive measured central systolic and diastolic pressures.

Alternatively, in another embodiment, the NIBP-calibrated peripheral waveform can be recalibrated prior to converting the peripheral waveform to the central aortic pressure waveform, e.g., using the transfer function method. In either embodiment, the method can be used to accurately estimate the central systolic and diastolic pressures with non-invasive peripheral measurements, using in part the transfer function method. The invention can also be used to shift and scale the non-invasive, central pressure waveform in the first embodiment, or the peripheral pulse waveform in the second embodiment, thereby resulting in a corrected (central or peripheral) waveform in which the cardiovascular features are preserved and the amplitude and SP and DP are accurate compared to invasive data.

The invention is applicable in particular to improving the systems described in the above incorporated O'Rourke and Qasem patents.

Referring to the first embodiment of the invention, the invention pertains generally to the following blood pressure measuring method. First, a brachial cuff device having an inflatable cuff is provided and the inflatable cuff is wrapped around the upper arm of a patient. The cuff is operated in oscillometric mode to measure the patient's brachial systolic blood pressure ($SP_B$) and brachial diastolic blood pressure ($DP_B$). A non-invasive sensor records an uncalibrated pulse waveform for a peripheral artery of the patient. The fidelity of the recorded, uncalibrated peripheral waveform must be sufficient to preserve the cardiovascular features of the waveform. The sensor can be, e.g., a tonometer, a brachial cuff or a photodiode sensor. The recorded, uncalibrated peripheral waveform is then NIBP-calibrated using at least two of the brachial systolic pressure ($SP_B$), brachial mean pressure ($MP_B$) and brachial diastolic pressure ($DP_B$). Then, in accordance with the first embodiment of the invention, the NIBP-calibrated peripheral pulse waveform having its cardiovascular waveform features preserved is converted to a NIBP-calibrated central pressure waveform having its cardiovascular waveform features preserved. This conversion is desirably accomplished using the transfer method described in O'Rourke and Qasem. The central aortic pressure waveform is then recalibrated based on one or more cardiovascular features in the NIBP-calibrated central pressure waveform so that the maximum and minimum of the recalibrated central pressure waveform correspond with invasive central systolic pressure (ICSP) and invasive central diastolic pressure (ICDP) respectively.

The recalibrating step can be accomplished in a number of ways. One desirable method involves the determination of one or more parameter values pertaining to the cardiovascular features of the NIBP-calibrated central pressure waveform, and then selecting one of multiple recalibration equations based on the determined values for the one or more parameters pertaining to the cardiovascular features of the NIBP-calibrated central pressure waveform. The selection of the appropriate recalibration equation can be based on a decision tree, e.g., which considers the patient's augmentation index (AIx), ejection duration (ED), heartrate (HR) and the percentage ratio of the area under the curve during diastole over the area under the curve during systole (AUCd/AUCs). While the selection of the recalibration equation can be made using a decision tree, other algorithms that correlate waveform features to the appropriate recalibration equations can be used, like support vector machines, linear and non-linear regression, neural networks and so on.

Preferably, the multiple recalibration equations have a common form with linear and nonlinear components but coefficients and scalar constants being selected to account for differences between invasive blood pressure measurements and non-invasive blood pressure measurements for the given combination of cardiovascular parameter values over the general population. The form of the recalibration equations in the first exemplary embodiment is a combination of linear and non-linear components, where the coefficients are selected so that the output from the recalibration equations provides an estimated waveform in which the maximum value matches data for invasively-measured central systolic pressure and the minimum of the outputted waveform matches data for the invasively-measured central diastolic pressure for each of the five identified situations. The inventor has discovered that a generalized linear transfer function is not capable of reliably and accurately mapping cuff measured NICBP to its invasive counterpart for the general population. The inventor has also discovered that it is best to determine the recalibration equations and the selection criteria for the specific NIBP device being used, for example by comparing non-invasive data measured with the device to simultaneously collected invasive data. In the exemplary embodiments of the invention, the form of the recalibration equations includes a non-linear component, such as a sigmoid function. Also, desirably, several sets of values for equation coefficients and constants are determined independently for the various recalibration equations in accordance with specific groups of data pertaining to the decision tree selection criteria. Machine learning techniques can be used to identify the criteria such that the recalibration equations for the respective groups of data result in reliably accurate recalibrated waveforms in which the maximum and minimum values are accurate estimates of invasively measured central systolic and diastolic pressure. An exemplary form of the recalibration equations implementing a sigmoid function is shown below:

where
$y(t)$ is the output waveform at time t
$P_i$, is na+nb+1 by 1 matrix of coefficients for recalibration equation i
$B_i$, is na+nb+1 by na+nb+1 square matrix of coefficients for recalibration equation i $$y(t) = ([u(t)\ u(t-1)\ \ldots\ u(t-na)\ y(t-1)\ \ldots\ y(t-nb)] \times P_i) + (a_i \times f([u(t)\ u(t-1)\ \ldots\ u(t-na)\ y(t-1)\ \ldots\ y(t-nb)] \times B_i + C_i))$$

$C_i$ is 1 by na+nb+1 matrix of coefficients for recalibration equation i
na, nb are the number of delay points for the input and output signals respectively,
$a_i$, $d_i$ are scalars (constants) for recalibration equation i
$u(t)$ is the input waveform at time t,
$u(t-1)$ is the input waveform at time t-1,
$u(t-na)$ is the input waveform at time t-na,
$y(t-1)$ is the output waveform at time t-1,
$y(t-nb)$ is the input waveform at time t-nb, and
and $f(\ )$ is a non-linear sigmoid function expressed as follows:

$$f(z) = \frac{1}{e^{-z}+1}.$$

As mentioned, the maximum and minimum values for the recalibrated central pressure waveform are accurate estimates of invasive central systolic (ICSP) and diastolic pressure (ICDP). These values can also be used to shift and scale the NIBP-calibrated central pressure waveform to result in the corrected central pressure waveform, where the maximum and minimum of the corrected central pressure waveform are set equal to the maximum and minimum of the recalibrated central pressure waveform respectively. The corrected central pressure waveform can be displayed as a trace or otherwise on a computer display screen in order to improve the clinical usefulness of the waveform analysis.

The second embodiment of the invention is similar in many ways to the first embodiment, with the primary difference being that the NIBP-calibrated peripheral waveform is recalibrated prior to converting the peripheral waveform to the central pressure waveform instead of recalibrating the central pressure waveform as described in connection from the first embodiment. Other differences should be apparent to those skilled in the art upon reviewing the following drawings and description thereof.

Those skilled in the art will appreciate that, while the invention has been described in terms of method steps, the invention is intended to be implemented in a blood pressure measuring system having signal and data processing capabilities sufficient to implement the disclosed methods.

In other embodiments of the invention, through collected data, the NIBP-calibrated peripheral or central waveform with cardiovascular related features can be categorized based on the waveform features and expected invasive SP and DP using machine learning algorithms like support vector machine, random forest, k-nearest classification, or boosting. These algorithms will provide equations that separate the waveforms based on its features into categories where each category represents ISP and IDP range of values. Another embodiment using another machine learning method like neural network such that collected data can be used to train a neural network with waveform features as inputs and the invasive SP and DP. The advantage of these embodiments is that they do not require specific recalibration equations and use a single general method to estimate invasive SP and DP from the NIBP-calibrated peripheral or central waveform with cardiovascular related features.

Other features and advantages of the invention may be apparent to those skilled in the art upon reviewing the drawings and the following description thereof.

DETAILED DESCRIPTION

Figure 1A:
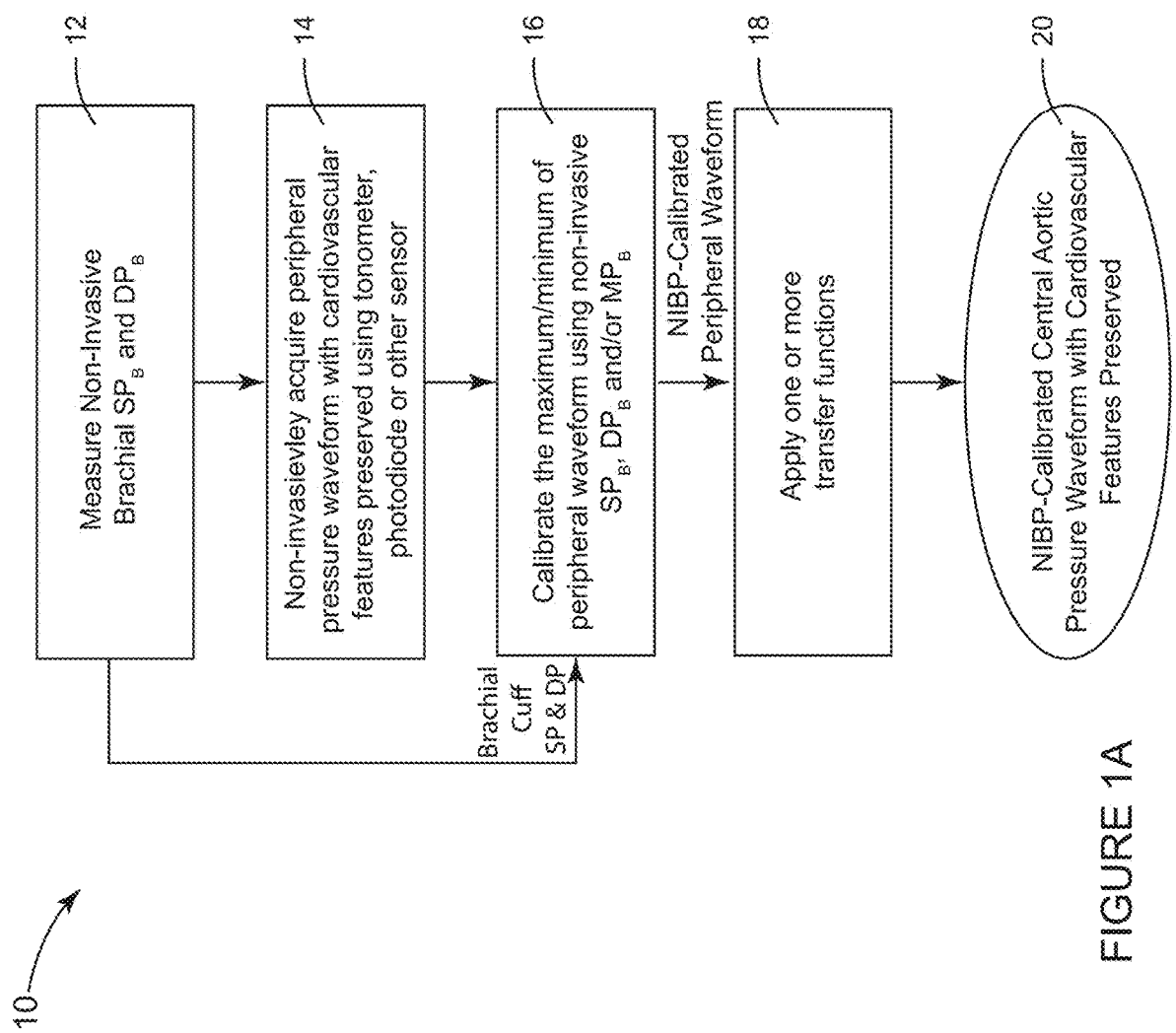
FIG. 1A is a block diagram illustrating the non-invasive measurement of a NIBP-calibrated central aortic pressure waveform with cardiovascular features preserved as known in the prior art and described in the above incorporated O'Rourke U.S. Pat. No. 5,265,011.
Figure 1B:
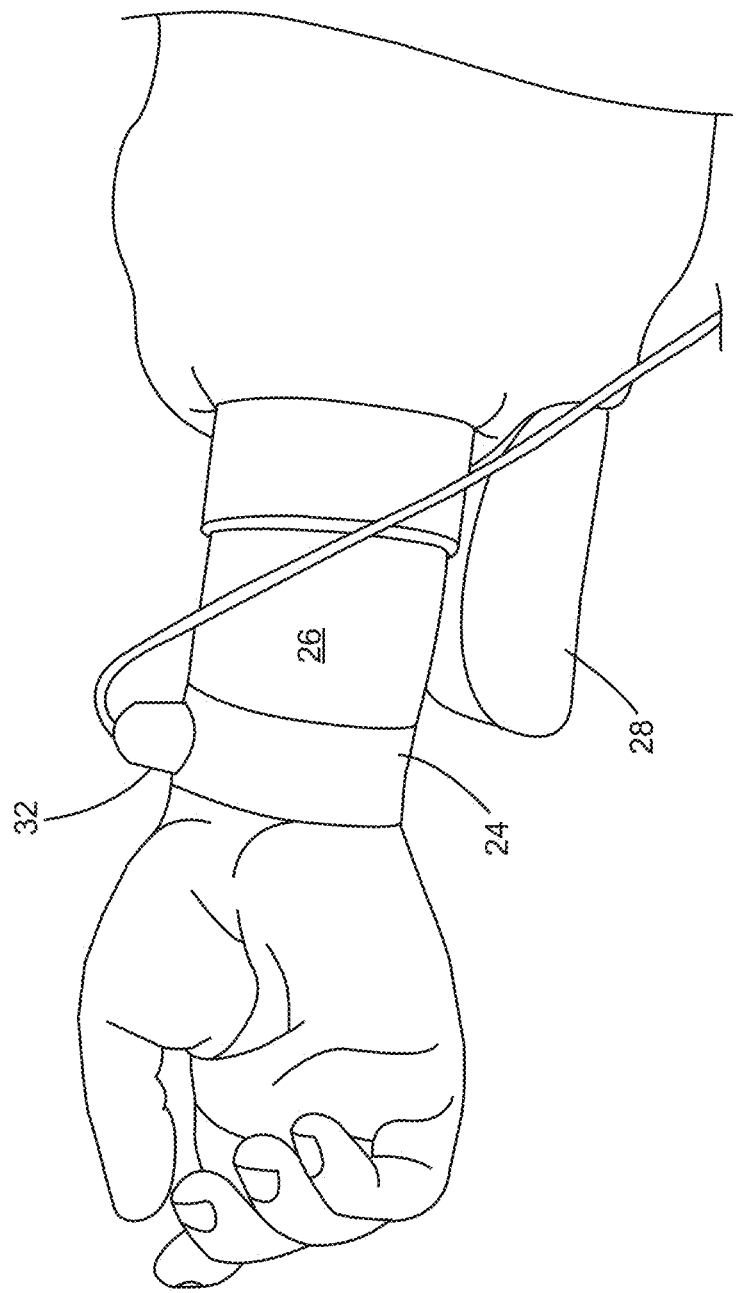
FIG. 1B illustrates the use of a tonometer to obtain an uncalibrated peripheral pressure waveform for the radial artery of a patient as is known in the prior art.

FIGS. 1A and 1B illustrate the prior art transfer function method 10 implemented in Applicant's SphygmoCor® system using a tonometer, which is described generally in the above incorporated O'Rourke patent. Applicant's SphygmoCor® system uses the transfer function method 10 to generate a calibrated central aortic pressure waveform with cardiovascular features preserved. The central pressure waveform as explained above is used clinically through central pressure waveform analysis to assess the cardiovascular system, and has also been widely used in research. The prior art transfer function method 10 shown in FIG. 1A begins, as depicted in block 12, by measuring the patient's brachial systolic pressure and diastolic pressure non-invasively using a cuff. The next step, block 14, is to acquire a peripheral pressure waveform with its cardiovascular features preserved. The peripheral pressure waveform is acquired non-invasively using a tonometer, photodiode or other sensor, and the raw waveform is calibrated, typically using the patient's SP and DP (and/or MP) as measured by a brachial cuff. Although FIG. 1A shows the brachial cuff systolic and diastolic pressures being measured (block 12) prior to obtaining the peripheral pulse waveform (block 14), those skilled in the art will understand that the cuff SP and DP can be measured after acquiring the raw peripheral pressure waveform. In accordance with the prior art, the SP and DP is normally measured using a brachial cuff device with an NIBP unit operating in oscillometric mode. Block 16 in FIG. 1A indicates that the non-invasively acquired, raw peripheral pressure waveform is calibrated using the cuff systolic, diastolic and/or mean pressure, which results in a NIBP-calibrated peripheral waveform. Mean pressure is often estimated by brachial cuff NIBP units, and some skilled in the art believe that it is more accurate to use this value when calibrating. The mean pressure is generally considered to be the mean pressure across the entire waveform, and therefore is roughly equal to about the diastolic pressure plus one-third of the difference between diastolic and systolic. The algorithms for determining mean pressure, however, vary among brachial cuff devices. It may be necessary after calibrating, according to Block 16, to further calibrate to adjust for differences that can occur from cuff to cuff due to the use of mean pressure to calibrate.

Referring still to FIG. 1A, one or more transfer functions are then applied to the calibrated peripheral pressure waveform, as shown in Block 18. The output from the transfer function(s) is a NIBP-calibrated central aortic pressure waveform with cardiovascular features preserved as depicted by reference number 20 in FIG. 1A. If the peripheral pressure waveform is a radial pressure waveform and is obtained with a tonometer, for example, the transfer function(s) is/are designed to convert the radial pressure waveform to the central aortic pressure waveform. FIG. 1B illustrates a tonometer device that includes a tonometer sensor or transducer 22 attached to a wrist strap 24. As shown in FIG. 1B, the strap 24 is preferably wrapped around the patient's wrist 26 so that the face of the tonometer sensor 22 is placed transcutaneous in a fixed location above the radial artery of the patient. Best results are obtained if the wrist is bent outward in a dorsiflex position, which pushes the radial artery towards the surface, thus making it easier to access. When using the dorsiflex position, the wrist 26 should rest on a small cushion 28 as illustrated in FIG. 1B. As is known in the art, the pressure of the tonometer against the patient's wrist may have to be adjusted in order to obtain an adequate waveform for the analysis.

As mentioned above and described in several of the references cited in the background portion of this application, the transfer function that is used commercially in the SphygmoCor® system using a tonometer is very accurate, but was determined on the basis of invasively measured radial artery pressure waveform data and invasively measured central aortic pressure waveform data. Errors can occur because calibrating the peripheral waveform using NIBP-measured systolic, diastolic and/or mean pressure with the cuff can lead to significant calibration errors in the NIBP-calibrated peripheral waveform, and consequently errors in the NIBP-calibrated central aortic pressure waveform 20, even though its cardiovascular features preserved 20. Even with calibration errors, the ability to observe the shape of the central aortic pressure waveform and analyze its cardiovascular features provides significant clinical information and is quite useful for analysis of a patient's condition. On the other hand, the ability to provide a central aortic pressure waveform with its cardiovascular features preserved and calibrated properly so that the maximum and minimum of the waveform provides reliable, close estimates of invasively measured central systolic (ICSP) and diastolic pressure (ICDP), as can be done with the invention described in connection with FIGS. 3 through 12, is a significant improvement.

Due to the inconvenience of using a tonometer, Applicant has developed the SphygmoCor® XCEL system which uses a brachial cuff to non-invasively acquire the patient's brachial pulse waveform, instead of a tonometer to measure a radial pressure waveform, see Qasem, Brachial Cuff, U.S. Pat. No. 9,314,170 issued Apr. 19, 2016, which has been incorporated by reference. While the Qasem patent should be referred to in order to attain a complete understanding of that invention, FIG. 2 herein provides a brief description of how the system in the Qasem patent operates.

Block 52 indicates that the patient's brachial SP, DP and/or mean pressure are measured using a brachial cuff in oscillometric mode. The cuff device as is known in the art includes an inflatable cuff, a tube, a pressure pump with the pressure control system, and a pressure sensor to measure the pressure in the inflated cuff. Arrow 66 indicates that the brachial cuff SP and DP are used in this example to calibrate the cuff waveform, block 60.

One of the discoveries in the Qasem patent was that by keeping the brachial cuff inflated to a constant pressure, data can be recorded representing the patient's raw brachial cuff volumetric displacement waveform, and this waveform can be filtered to obtain data representing the uncalibrated brachial arterial pulse waveform in which the cardiovascular waveform features are preserved. The brachial cuff waveform is not a pressure waveform, and another discovery in the Qasem patent was that the pressure of the inflated brachial cuff around the patient's upper arm affects the shape of the brachial pulse waveform. In particular, the constant cuff inflation pressure when recording the raw brachial cuff volumetric displacement waveform data needs to be set with respect to the patient's measured NISP and NIDP in order for the waveform data to correlate correctly when establishing (a) suitable transfer function(s). Block 54 in FIG. 2 indicates that the inflated cuff pressure is selected at a pressure less than NIDP, between NIDP and NISP, or above NISP (depending on the procedure used when calculating the non-invasive waveform data to calculate the one or more transfer functions used in block 62). In accordance with the Qasem reference, the cuff pressure should not be set at or near the DP or SP measured by the cuff in the oscillometric mode.

Assuming that the cuff is inflated to a percentage of NIDP in block 54, block 56 indicates that the cuff pressure is maintained at that constant level in order to acquire or record the raw cuff waveform. Block 58 indicates that the raw cuff waveform is processed through a high pass filter and low pass filter or a band pass filter to produce a pre-calibrated brachial cuff volumetric displacement waveform. The filters are selected so that the pre-calibrated cuff waveform preserves the cardiovascular features present in the patient's brachial artery. The filtering of the raw cuff waveform is dependent on the particular cuff device and its control unit, but should be selected so that the raw waveform includes identifiable cardiovascular features such as the waveform foot, the first and second systolic peak and the incisura. In block 60, the brachial cuff SP and DP are used to calibrate the filtered, pre-calibrated cuff waveform, which results in a NIBP-calibrated cuff waveform. In accordance with the Qasem patent, block 62 indicates that one or more transfer functions, accounting for the inflated cuff pressure when the waveform is recorded, are applied to the NIBP-calibrated cuff waveform to obtain the calibrated aortic pressure waveform with cardiovascular features preserved.

Figure 2:
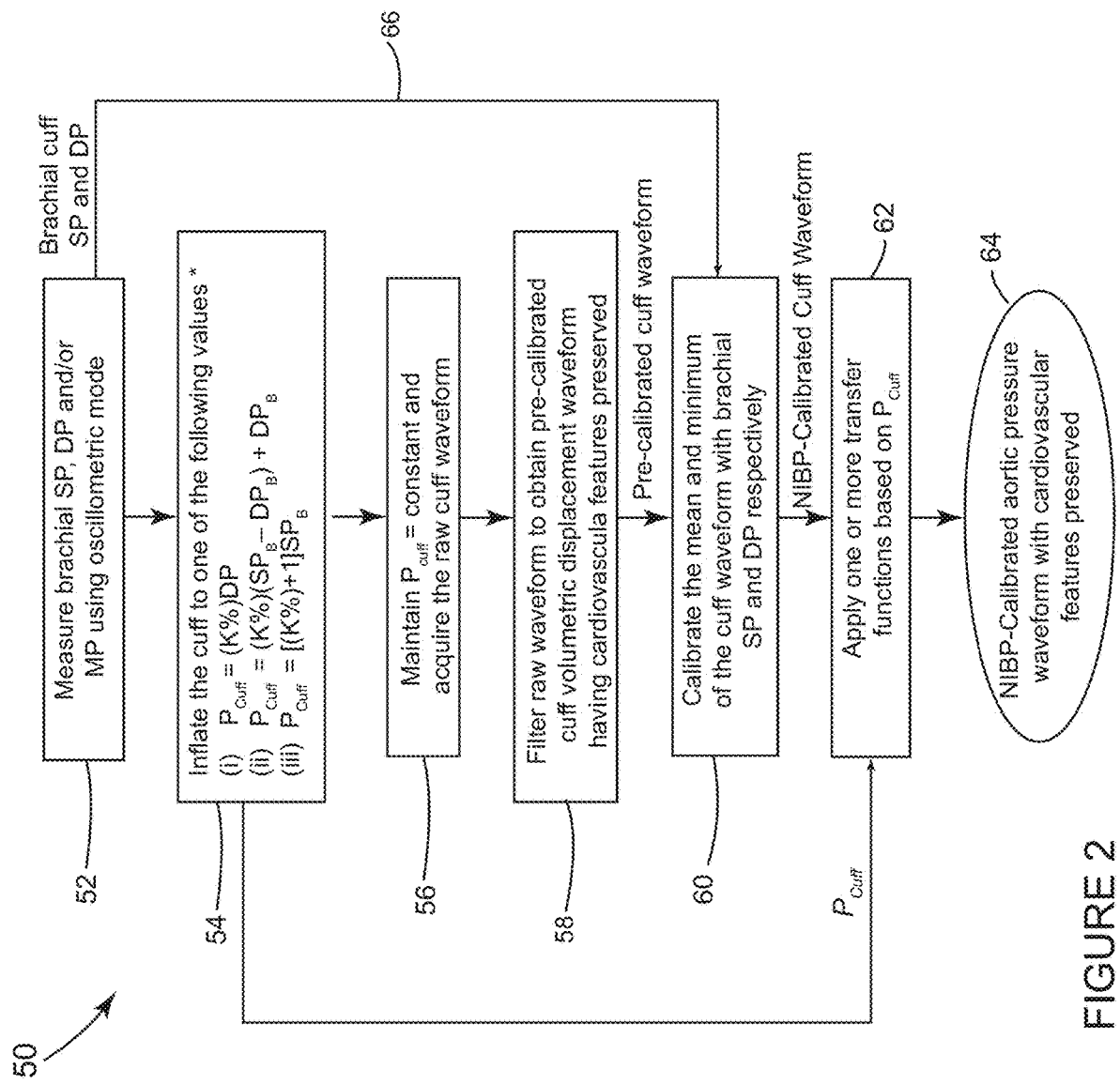
FIG. 2 is a block diagram illustrating the non-invasive measurement of a NIBP-calibrated central aortic pressure waveform with cardiovascular features preserved, wherein a peripheral waveform is measured with a brachial cuff as known in the prior art and described in the above incorporated Qasem U.S. Pat. No. 9,314,170.

Similar to the prior art system described in FIGS. 1A and 1B, testing has shown that Applicant's SphygmoCor XCEL system which operates in accordance with the incorporated Qasem patent and FIG. 2 provides NIBP-calibrated central aortic pressure waveforms with an accurate depiction of shape, but the waveform tends to overestimate central diastolic pressure and underestimate central systolic pressure due to calibration errors stemming from the use of NIBP-approved cuff devices in oscillometric mode to determine brachial SP and DP used in the initial calibration.

Figure 3:
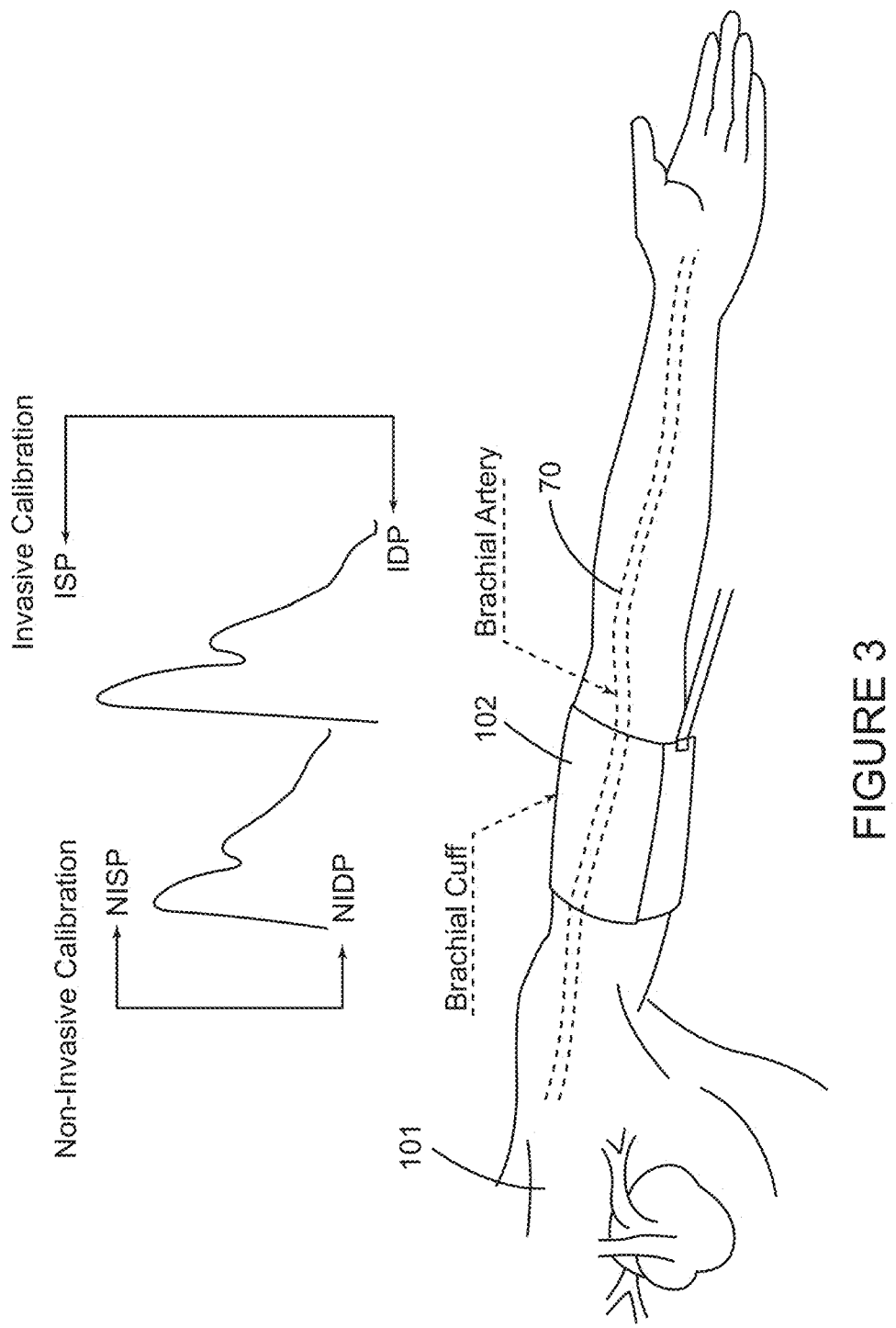
FIG. 3 illustrates the difference between non-invasive systolic and diastolic pressure (NISP/NIDP) measured by a brachial cuff, and invasively measured systolic and diastolic pressure (ISP/IDP) in the brachial artery.

Referring to FIG. 3, as mentioned, there can be significant differences between invasive and non-invasive brachial arterial blood pressure values. FIG. 3 illustrates a brachial cuff 102 wrapped around the upper arm of a patient 101 for the purpose of non-invasively measuring the patient's systolic and diastolic blood pressure in the brachial artery 70. The non-invasively measured systolic blood pressure is identified in FIG. 3 as NISP, and the non-invasively measured diastolic blood pressure is identified as NIDP. FIG. 3 also illustrates measuring the patient's systolic and diastolic pressures in the brachial artery 70 invasively (e.g., using a pressure sensor with a catheter inserted into the patient's arm and brachial artery 103). The invasively measured systolic blood pressure is identified in FIG. 3 as ISP, and the invasively measured diastolic blood pressure is identified as IDP. As mentioned previously, invasively measured pressure ISP and IDP are considered to be the gold standard for clinical and research analysis and present day inflated cuff, oscillometric systems typically underestimate systolic brachial pressure (i.e., NISP<ISP) and overestimate diastolic brachial pressure (i.e., NIDP>IDP). The aim of the current invention is to reduce or eliminate the difference prevalent between invasive measurements and non-invasive measurements.

Figure 4:
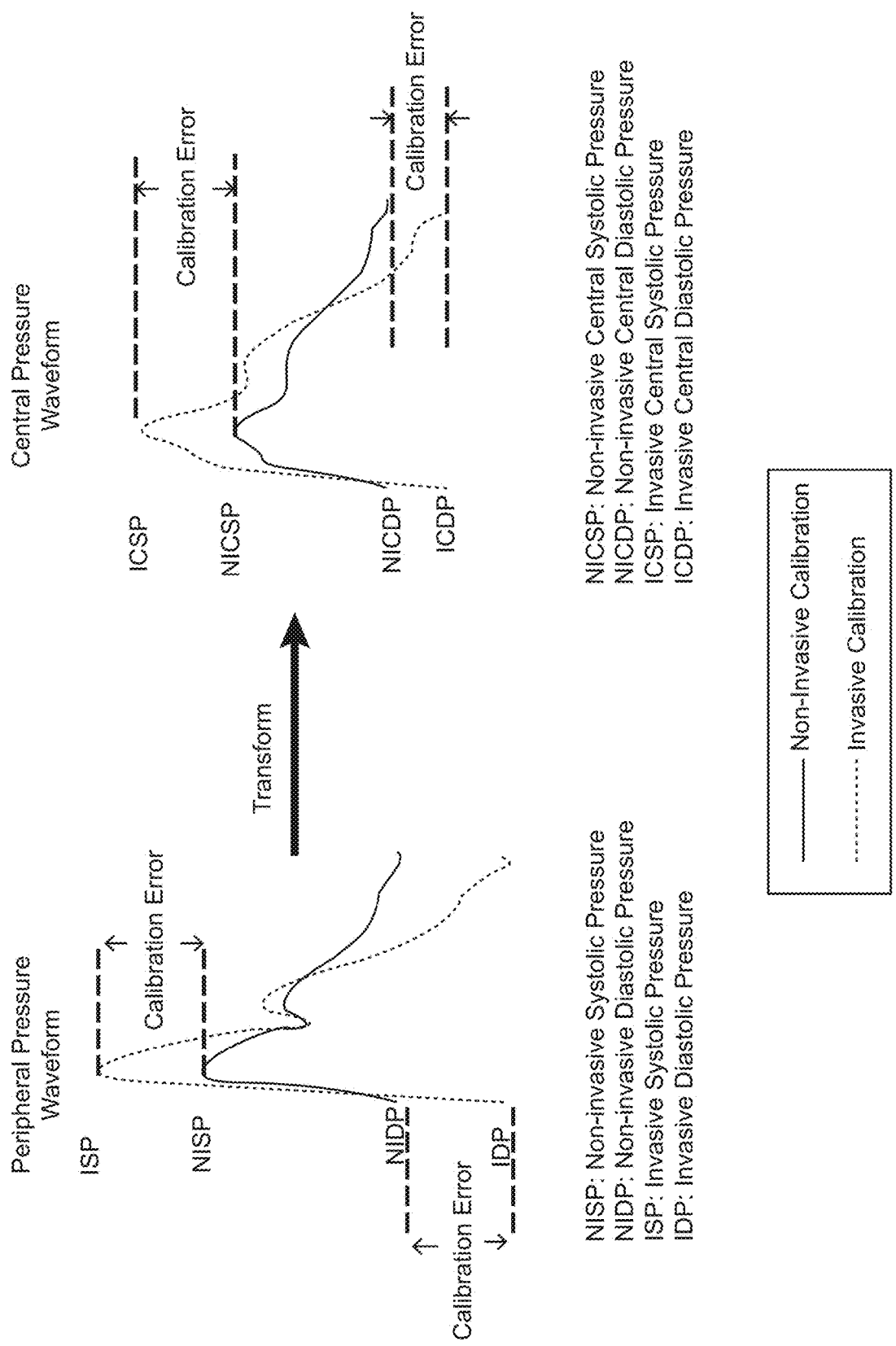
FIG. 4 demonstrates the effect of peripheral waveform calibration error due to the difference between NISP/NIDP and ISP/IDP on the estimated central pressure waveform, namely non-invasive central systolic/diastolic pressure (NICSP/NICDP) differs from the invasive central systolic/diastolic pressure (ICSP/ICDP) respectively due to the calibration error.

FIG. 4 illustrates the effect of using cuff measured NIBP systolic pressure (NISP) and diastolic pressure (NIDP) if the cuff device overestimates NIDP and underestimates NISP. Referring to the peripheral pressure waveforms on the left side of FIG. 4, the solid line depicts a NIBP-calibrated peripheral pressure waveform that is calibrated using NISP and NIDP as is now common in the art. The dashed line on the left side of FIG. 4 represents the peripheral pressure waveform if it were calibrated using ISP and IDP, or if it were measured invasively. The goal of the current invention is to eliminate the effect of the calibration error illustrated in FIG. 4. When the peripheral pressure waveforms on the left are transformed using one or more transfer functions, the resulting waveforms are shown on the right side of FIG. 4. On the right side of FIG. 4, the solid line depicts a central pressure waveform based on the NIBP-calibrated peripheral waveform, whereas the dashed line depicts the central pressure waveform as calibrated to invasively measured SP and DP. The shapes of the two central waveforms are generally similar except for calibration errors with respect to actual measurements of invasive central diastolic pressure (ICDP) and invasive central diastolic pressure (ICSP). Note that the calibration error in this example is more than simply an issue of scaling inasmuch as the calibration error with respect to diastolic pressure for the peripheral waveform is different than for the central waveform. Note that the amount of calibration error in FIG. 4 between the peripheral waveform and the central waveform appears similar for SP; the calibration error for SP can rise as well depending on the underlying shape of the waveform. The aim of the current invention is to reduce or eliminate the calibration error demonstrated in FIG. 4 that is prevalent between invasive measurements and non-invasive measurements.

Figure 5:
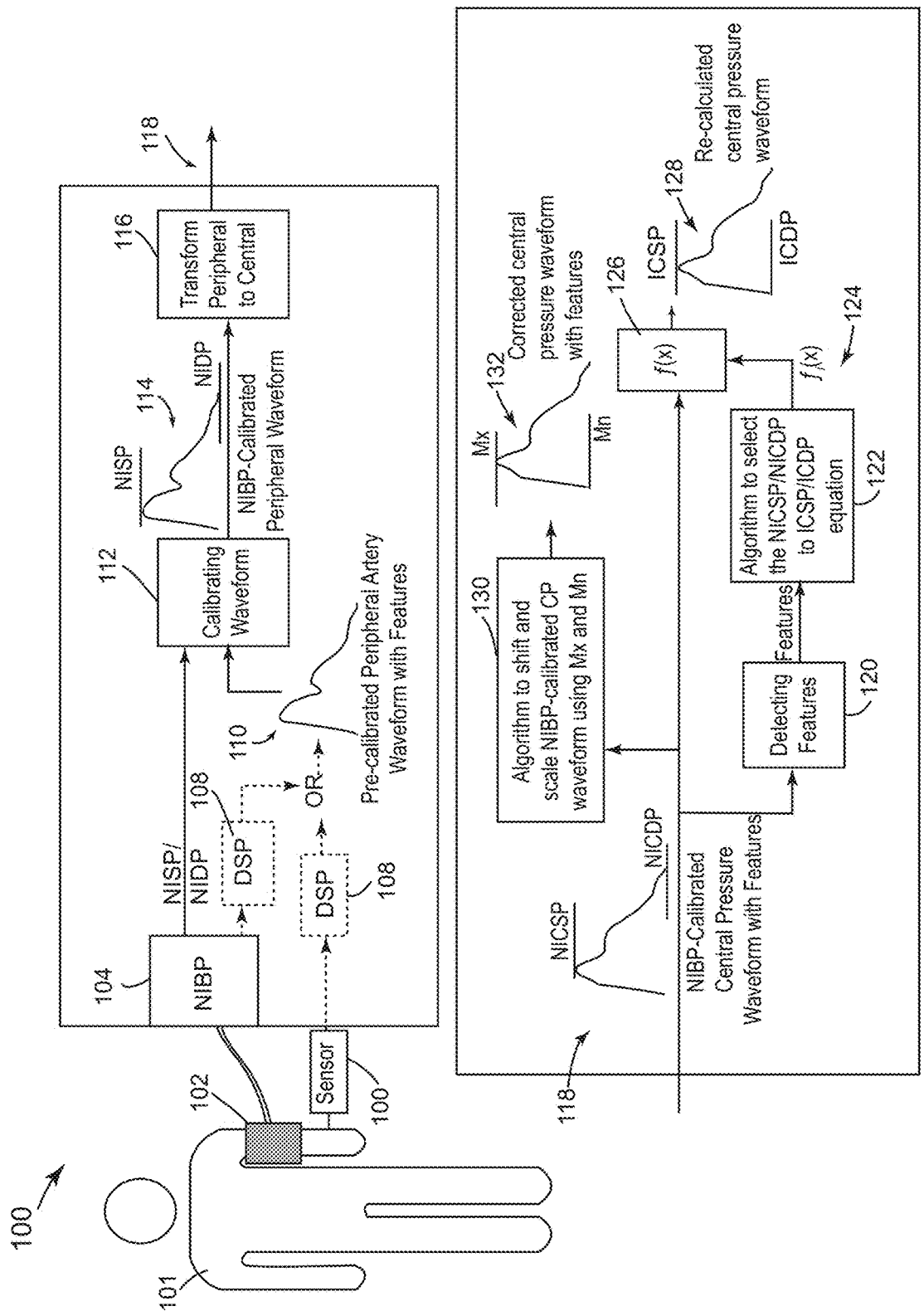
FIG. 5 is the schematic drawing illustrating a first embodiment of the invention, which records a non-invasive peripheral waveform, measures NISP and NIDP using a brachial cuff device, estimates ICSP and ICDP and optionally provides a scaled central aortic pressure waveform in which the maximum and the minimum set to the estimated ICSP and ICDP.

FIG. 5 illustrates a system 100 configured in accordance with one exemplary embodiment of the invention. The system 100 in FIG. 5 includes a non-invasive blood pressure unit 104 (NIBP unit 104), which is the same as or similar to a conventional brachial cuff "oscillometric" blood pressure device. The NIBP unit 104 includes, e.g., a cuff 102, pressure tube, an air pressure control, and a pressure sensor for sensing the pressure in the cuff 102. The NIBP unit 104 also includes control algorithms which operate in the oscillometric mode to determine NISP and NIDP, as is common in the art. With a cuff 102 wrapped around the patient's upper arm (including the brachial artery 70), the NIBP unit 104 performs an oscillometric brachial blood pressure measurement resulting in a value for the non-invasive brachial systolic pressure (NISP) and non-invasive brachial diastolic pressure (NIDP). FIG. 5 also shows a sensor 106, like a tonometer or photodiode sensor, to record non-invasive arterial pulse waveform from a peripheral artery such as the radial or brachial artery, or an artery in the finger. The signal from the sensor 106 is sent to a digital signal processor 108, which may need to filter the signal to ensure that the cardiovascular waveform features are preserved and/or convert the waveform to digital data for processing. Alternatively to using a separate peripheral sensor 106, the NIBP unit 104 can record the raw oscillometric cuff waveform while the cuff 102 is inflated to a constant pressure (below NIDP, between NIDP and NISP or above NISP) as described above with respect to FIG. 2. The signal from NIBP unit 104 representing the raw oscillometric cuff waveform is sent to a digital signal processor 108, which filters the signal to ensure that the cardiovascular waveform features are preserved and converts the waveform to digital data for processing. As discussed above, the raw cuff waveform is processed through a high pass filter and low pass filter or a band pass filter to produce a pre-calibrated brachial cuff waveform with cardiovascular related features preserved. This waveform is a brachial cuff volumetric displacement waveform, which contains and preserves the cardiovascular features present in the patient's brachial artery pressure waveform, however, the amplitude of the waveform needs to be calibrated. As mentioned, the pressure of the inflated cuff will affect the shape of the recorded waveform, and therefore it is important that the cuff be inflated with respect to NISP and NIDP consistent with the inflation of the cuff for the data collected to determine the recalibration equations discussed below as well as the transfer function(s) for converting to the central pressure waveform. For example, if the recalibration equations and transfer function(s) are determined based on data collected with the cuff inflated below NIDP for the test population, then the raw brachial (volumetric displacement) waveform should be collected with the cuff inflated below the patient's NIDP. It is preferred that the inflated cuff pressure have a 10% difference or more compared the patient's DP in order to avoid borderline effects. The same considerations apply with respect to both DP and SP in the case that the recalibration equations and/or transfer function(s) are determined based on data collected with the cuff inflated between NIDP and NISP for the test population, or with respect to SP in the case that the recalibration equations are determined based on data collected with the cuff inflated above NISP for the test population. In some applications, it may be necessary to maintain the pressure of the inflated cuff between NIDP and NISP in order to ensure sufficient resolution of the captured waveform.

While the filtering of the raw cuff waveform is dependent on the particular cuff device, the cuff pressure relative to NISP or NIDP and NIBP unit 104 used, the filtering in an exemplary embodiment uses a low pass filter with cutoff frequency between 30 to 40 Hz, and high pass filter with pass frequency between 0.7 to 1 Hz has been found suitable to capture a raw waveform in which the cardiovascular features, including the foot, first systolic peak, second systolic peak and incisura, are preserved in the data. The purpose of the low pass filter is to preserve volume, pressure or flow signal frequencies that are related to physiological function and eliminate noises related to environmental inferences such as power sources noise. The choice of the low pass cutoff frequency is based on the fact that all physiological features in a pressure, volume, flow waveforms are within 25 Hz of the signal spectrum (See e.g., FIG. 26.21 in W. Nichols and M. O'Rourke, "McDonald's Blood Flow in Arteries: Theoretical, Experimental and Clinical Principles", $5^{th}$ Edition). The purpose of the high pass filter is to eliminate low frequencies related to artifacts noise as a result of arm movements, breathing effect or the tube and cuff reaction to the compliance to pressure. These low frequency artifacts, which cause signal baseline drift and can dampen signal shape, are usually below 1 Hz, hence the high pass filter pass frequency. Both filters, which can be implemented as a Chebyshev type filters with pass band ripple or stop band ripple of –3 dB, can be combined into one band pass filter where it pass all frequencies between 0.7 to 40 Hz. The operations after the NIBP unit 104 in FIG. 5 are preferably implemented in a digital signal processor 108, or other computing device. However, the electronic filters discussed in connection with acquiring the raw waveform can be analog or digital, or a combination of both.

The recorded pre-calibrated peripheral waveform 110, whether recorded from the NIBP cuff 102, NIBP unit 104 or from another peripheral artery sensor 106, is processed preferably in digital signal processor 108 in order to produce a NIBP-calibrated, peripheral waveform with cardiovascular related features 114. The electronic filters discussed can be analog or digital, with analog-to-digital conversion.

Block 112 in FIG. 5 depicts both the pre-calibrated peripheral waveform 110 (with features preserved) and the NISP and NIDP values being entered into an algorithm (e.g. software code) that calibrates the pre-calibrated peripheral waveform 110 so that the maximum and minimum values of waveform 110 are equivalent to NISP and NIDP, respectively. This initial calibration results in a NIBP-calibrated peripheral waveform (with cardiovascular features preserved) as indicated by reference number 114 in FIG. 5. In accordance with the invention, it is possible to calibrate the pre-calibrated peripheral waveform using a mean pressure (NIMP), such as calibrating with NIDP and NIMP to be equivalent to the minimum and mean of the pre-calibrated peripheral respectively. The NIBP-calibrated peripheral waveform 114 corresponds to the solid non-invasive line on the left side of FIG. 4, and may include calibration error to the extent that the NIBP unit 104 does not accurately estimate the patient's brachial systolic and diastolic pressures.

Block 116 in FIG. 5 indicates that in this embodiment the one or more transfer functions convert the NIBP-calibrated peripheral waveform 114 to a NIBP-calibrated aortic pressure waveform 118 using one or more generalized transfer functions. The one or more generalized transfer functions represent the harmonic ratio in amplitude and phase to transform the peripheral waveform to the aortic pressure waveform. If the peripheral waveform is derived from the raw brachial cuff volumetric displacement waveform, then the one or more transfer function(s) need(s) to be designed to be used when the brachial cuff is inflated to a constant pressure within the appropriate pressure range, (i.e, $P_{cuff}$ below NIDP, or $P_{cuff}$ between NIDP and NISP, or $P_{cuff}$ above NISP for the reasons described in the incorporated Qasem patent). The NIBP-calibrated central pressure waveform 118 corresponds to the solid non-invasive line on the right side of FIG. 4, and consequently may include calibration error in the event that the NIBP-calibrated peripheral waveform 114 contains calibration error.

Figure 6:
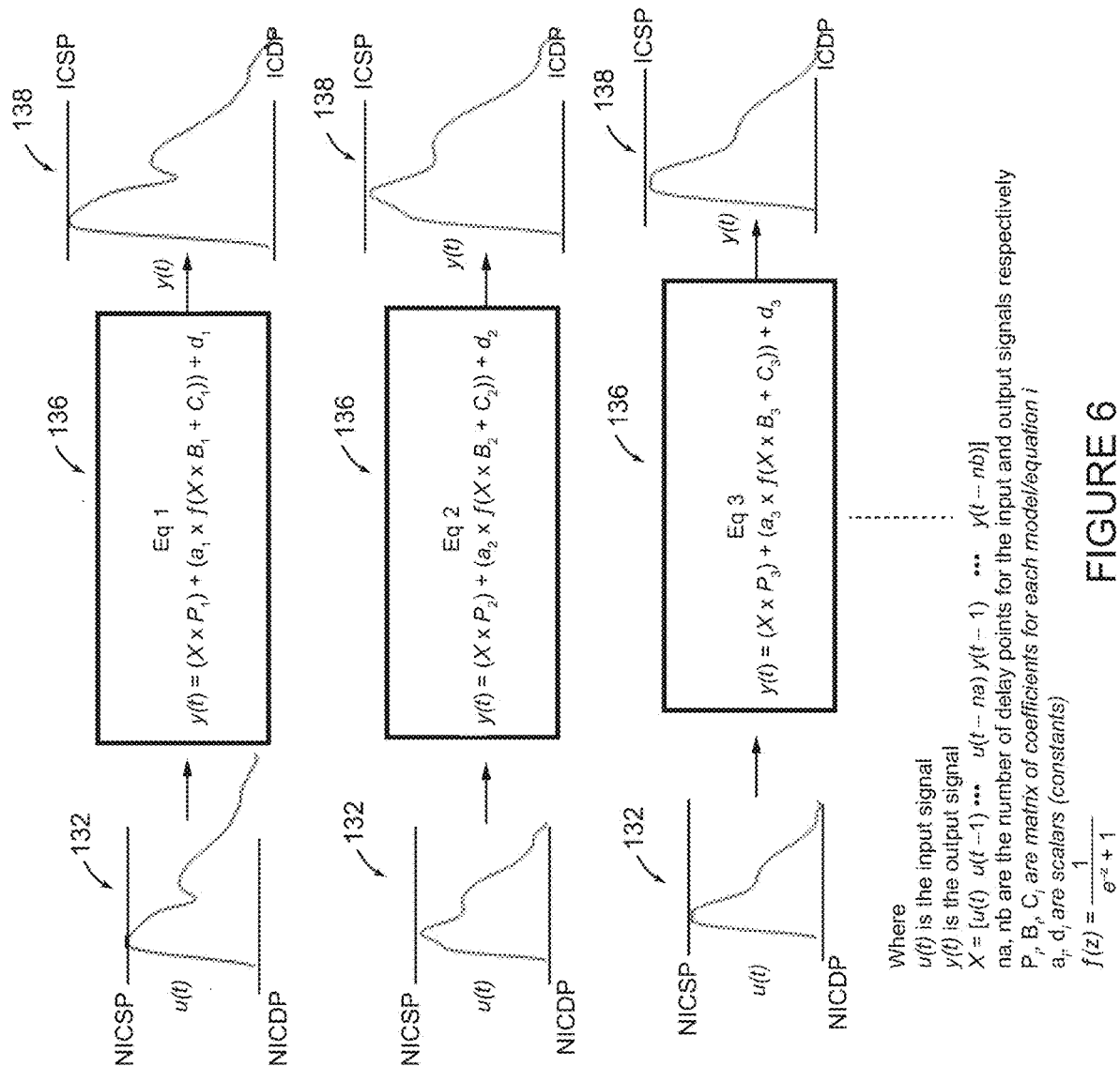
FIG. 6 shows an exemplary form of non-invasive to invasive central blood pressure waveform recalibration equations for central pressure waveforms having different waveform shapes.

The software depicted in block 120 determines parameter values for cardiovascular related features of the NIBP-calibrated central pressure waveform 118. The specific cardiovascular features used in this exemplary embodiment are explained in connection with FIG. 7. Referring still to FIG. 5, the determined feature parameter values from block 120 are the input for a selection algorithm, block 122, that determines which recalibration equation $f_i(x)$, reference number 124, should be used to recalibrate the NIBP-calibrated central pressure waveform 118 in terms of invasive central pressure (ICSP/ICDP) instead of non-invasive central pressure (NICSP/NICDP). Examples of a selection algorithm 122 and recalibration equations 124 are shown in FIG. 8 and FIG. 6 respectively, and are discussed in more detail below. Block 126 in FIG. 5 indicates that the selected recalibration equation 124 operates on the NIBP-calibrated central pressure waveform 118, to produce a recalibrated waveform 128 where the maximum (Mx) and the minimum (Mn) values provide accurate estimates of the invasive central systolic pressure (ICSP) and invasive central diastolic pressure (ICDP), respectively. While the waveform 128 provides accurate estimates of ICSP and ICDP, the shape of the waveform 128 may be unnecessarily distorted compared to the shape of the NIBP-calibrated central pressure waveform 118 and therefore may not be optimal for central pressure waveform analysis in a clinical or research setting. Still referring to FIG. 5, block 130 depicts the software using Mx and Mn from the recalibrated central pressure waveform 128 as input to shift and/or scale the NIBP-calibrated central pressure waveform 118, thereby resulting in a corrected central pressure waveform 132. The corrected central pressure waveform 132 accurately embodies the shape of the central pressure waveform and the amplitude of the central pressure waveform.

Data of invasive central aortic pressure alongside along side recording of non-invasive estimated central pressure measurements were used to calculate the non-invasive to invasive blood pressure recalibration equations 124. More specifically, data was collected from 150 patients providing a representation of the general population. More specifically, data was collected from 150 patients with wide range of brachial SP, DP (SP range from 88 to 216 mmHg and DP range from 40 to 93 mmHg) and heart rate (from 41 to 102 beats per minute) providing a representation of the general population. The collected data included invasively measured central pressure waveform data (collected through a fluid filled catheter with properly tested frequency response for every measurement) and contemporaneously collected NIBP-measured SP and DP, filtered NIBP brachial waveform data, central pressure waveform data estimated from filtered NIBP-calibrated brachial waveform data and invasive central pressure waveform and ICSP and ICDP data. The cuff was inflated at 10% of the patient's NIDP to collect the filtered NIBP brachial waveforms. Referring to FIG. 6, a method of system identification was used to establish the coefficients for proposed recalibration equations 136. In the exemplary embodiment, a system identification method, which constitute linear and non-linear components such as non-linear sigmoid function was used. In general, the non-invasively collected cuff data is filtered and NIBP calibrated (like block 112 in FIG. 5) to obtain a NIBP-calibrated brachial cuff waveform (like 114 in FIG. 5), then transformed using the transfer function method to obtain a NIBP-calibrated central pressure waveform (like 118 in FIG. 5, where the maximum is NICSP and the minimum is NICDP). The NIBP-calibrated central pressure waveform derived from the collected cuff data is the input 134 for the proposed recalibration equations 136. Invasively collected data 138 for the central artery, necessarily having its maximum and minimum values equal to ICSP and ICDP, respectively, is the output 138 of the proposed recalibration equations 136. Given the known input 134 and output 138 from the collected data, recalibration equations 136 with unknown coefficients are proposed. Then, the coefficients are estimated such that the difference between the equation output and the data collected for the invasive blood pressure measurements is minimized. The recalibration equations can theoretically be linear or non-linear or combination of both types, however, it has been found that using a non-linear component produces more accurate results. In the exemplary embodiment of the invention, the proposed form has linear and non-linear components and can be expressed as follow:

$$y(t) = (X \times P_i) + (a_i \times f(X \times B_i + C_i)) + d_i \quad [1]$$

where y(t) is the output waveform at time t $P_i$, $B_i$, $C_i$ are matrices of coefficients for each recalibration equation i, and $a_i$, $d_i$ are scalars (constants) for each recalibration equation i.

Further, vector X in equation [1] is a vector of delayed input and output values which can be represented as follow:

$$X = [u(t) u(t-1) \ldots u(t-na) y(t-1) \ldots y(t-nb)] \quad [2]$$

where u(t) is the input waveform at time t, u(t−1) is the input waveform at time t−1, u(t−na) is the input waveform at time t−na, y(t−1) is the output waveform at time t−1, y(t−nb) is the input waveform at time t−nb, and na, nb are the number of delay points for the input and output signals respectively.

In equation [1], f( ) is a non-linear function which in this example is a sigmoid function expressed as follow:

$$f(z) = \frac{1}{e^{-z} + 1}$$

To illustrate how the equation works, assume that na and nb are equal to 1, then vector X in equation [1] will be $$X = [u(t) u(t-1) y(t-1)] \quad [3]$$

Accordingly, $$P_i = \begin{bmatrix} p_1 \\ p_2 \\ p_3 \end{bmatrix} \quad [4]$$

$$B_i = \begin{bmatrix} b_{1,1} & b_{1,2} & b_{1,3} \\ b_{2,1} & b_{2,2} & b_{2,3} \\ b_{3,1} & b_{3,2} & b_{3,3} \end{bmatrix} \quad [5]$$

$$C_i = [c_1 \ c_2 \ c_3] \quad [6]$$

Then, substituting equations [3] to [6] into equation [1], the result will be $$y(t) = \left( [u(t) \ u(t-1) \ y(t-1)] \times \begin{bmatrix} P_1 \\ P_2 \\ P_3 \end{bmatrix} \right) + \quad [7]$$

$$\left( a_i \times f \left( \left( [u(t) \ u(t-1) \ y(t-1)] \times \begin{bmatrix} b_{1,1} & b_{1,2} & b_{1,3} \\ b_{2,1} & b_{2,2} & b_{2,3} \\ b_{3,1} & b_{3,2} & b_{3,3} \end{bmatrix} \right) + \right.$$

$$\left. [c_1 \ c_2 \ c_3] \right) \right) + d_i$$

The goal of the system identification method is to estimate coefficient matrices $P_i$, $B_i$, $C_i$ and the constants $a_i$, $d_i$ to minimize the difference between estimated output and the collected invasive data 138.

Applying the system identification method on invasive data collected for a sampling of the general population in this exemplary embodiment results in five (5) different recalibration equations 136 (see FIG. 6) that can be implemented on the general population. In other words, the final form of the proposed recalibration equations 136 in FIG. 6 corresponds to the recalibration equations 124 programmed in to the system 100 in FIG. 5. The final form of the proposed recalibration equations 136 is determined for different groupings of input 134 and output 138 waveform data, in which the groupings are based on waveform feature parameters determined by applying the system identification method. In this exemplary embodiment, the selection algorithm 122 is a decision tree, see FIG. 8, which determines which recalibration equation 124 should be used based on waveform features.

Figure 7:
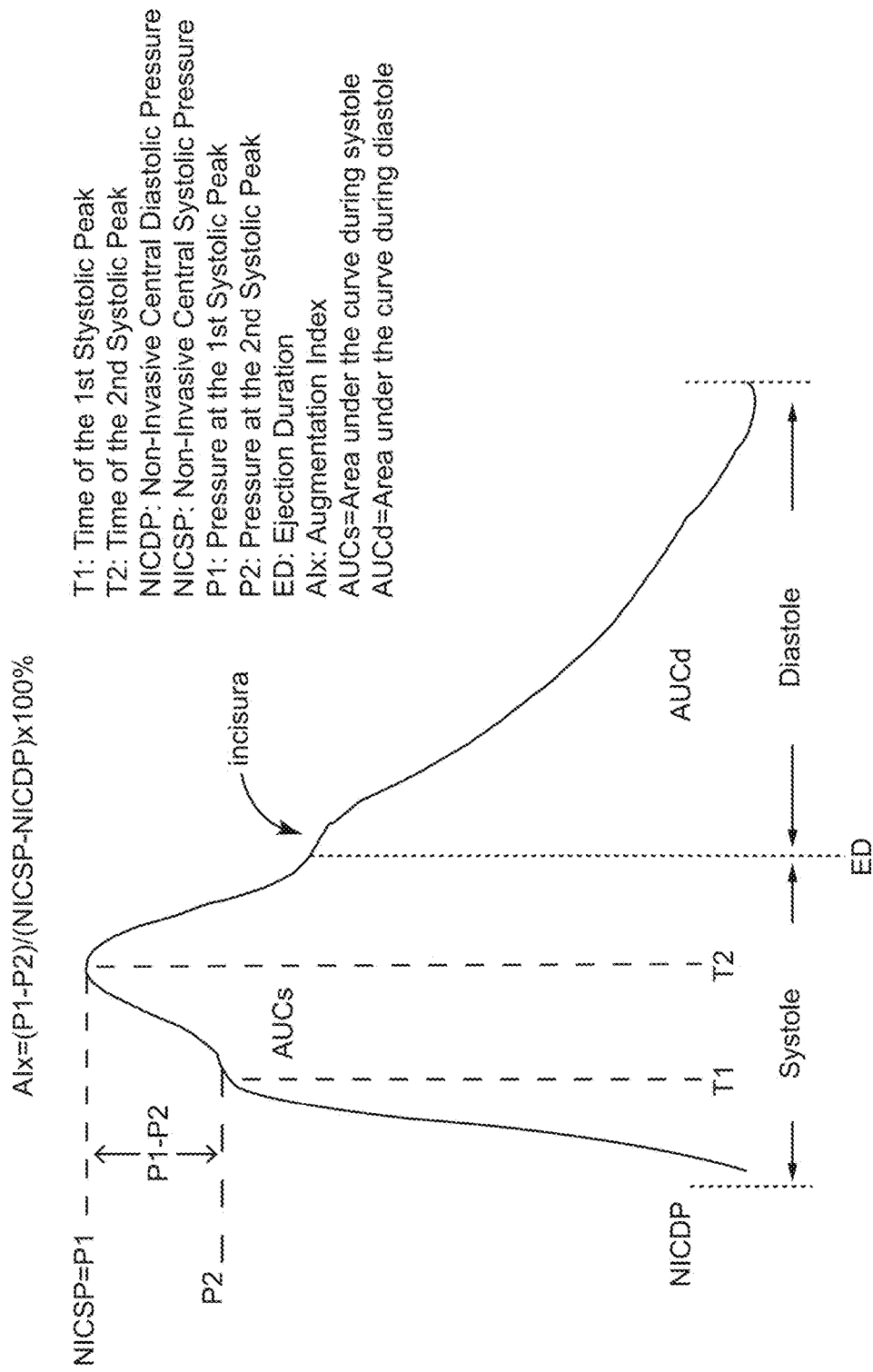
FIG. 7 shows and defines certain cardiovascular features of an initially calibrated (NICSP/NICDP) central pressure waveform.
Figure 8:
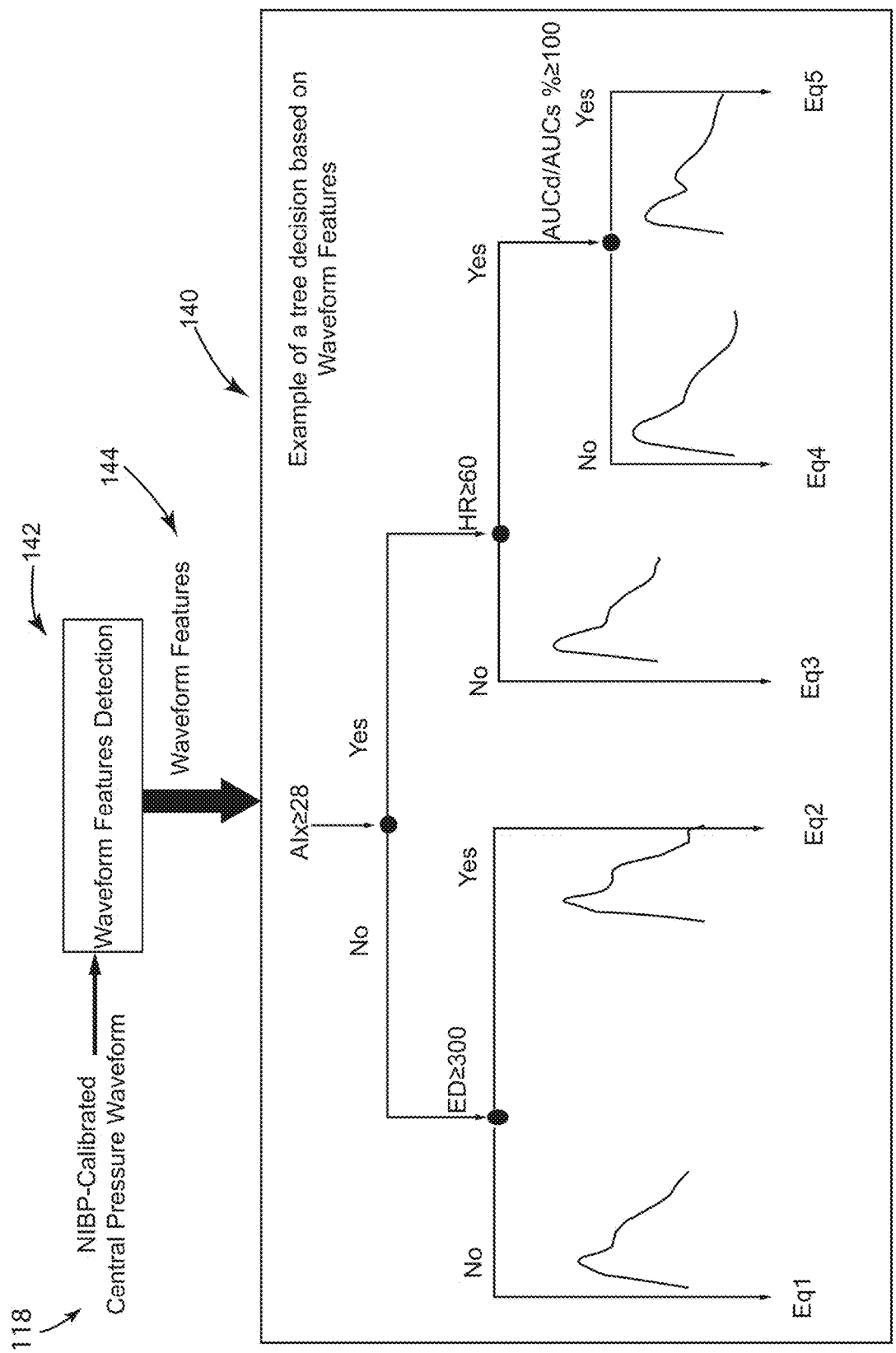
FIG. 8 shows an example decision tree based on cardiovascular features of NIBP-calibrated (NICSP/NICDP) central pressure waveform that determine which non-invasive to invasive central blood pressure recalibration equation should be used.

FIG. 7 describes some of the waveform cardiovascular related features, which are used as inputs to the selection algorithm 122 in this exemplary embodiment. The cardiovascular related features and others can be detected or calculated, e.g., using the through derivative method as described in O'Rourke U.S. Pat. No. 5,265,011 which is incorporated by reference, or other suitable mathematical method in time or frequency like wavelet analysis. Exemplary features that can be used by the selection algorithm include, for example, NICSP, NICDP, AIx, AUCs/AUCd, P1, P2, T1, T2, and ED as described in FIG. 7. Other features like mean pressure, heart rate, cardiac period and slope of the systolic upstroke, which also can be detected from the NIBP-calibrated central pressure waveform, can also be used as input to the algorithm.

The parameters and threshold values for the parameters in order to construct the decision tree selection algorithm, which selects the appropriate recalibration equation 122 to recalibrate from NICSP/NICDP to ICSP/ICDP based on the recorded NIBP-calibrated waveform characteristics, can be determined by training decision tree algorithm to determine the threshold and structure of the tree. However, the recalibration equations and selection algorithm, or other suitable algorithm for recalibration conversion, can be developed using other types of machine learning such as support vector machine, linear and nonlinear regression, and neural network. In any event, the overall purpose is to provide an algorithm in which data representing a NIBP-calibrated central pressure waveform with cardiovascular features preserved serve as the input, and the maximum and minimum value of the output waveform closely estimates ICSP and ICDP, respectively, based on known population data.

FIG. 8 depicts the operation of an exemplary selection algorithm 140. Suitable selection algorithms may be somewhat more complicated than the illustrative algorithm shown in FIG. 8. The illustrative selection algorithm in FIG. 8 is in the form of a decision tree that is used to determine the appropriate recalibration equation based on the detected or calculated waveform features or parameters. The recalibration equations are labelled Eq1, Eq2, Eq3, Eq4 and Eq5 in FIG. 8. Block 142 in FIG. 8 depicts pulse waveform features 144 being detected from the NIBP-calibrated central pressure waveform 118. As mentioned, suitable feature detection methods block 142, include the derivative method or other mathematical methods in time or frequency domain. The values detected or calculated pertaining to the waveform features 144 are the input to the decision tree 140, which in this example serves as the selection algorithm 122 in FIG. 5. The decision tree 140 decides which recalibration equation Eq1, Eq2, Eq3, Eq4 or Eq5 to use according to the values of the detected or calculated waveform features. For purpose of illustration, in FIG. 8, one of five NICSP/NICDP to ICSP/ICDP recalibration equations (Eq1, Eq2, Eq3, Eq4 or Eq5) is selected based on values of AIx, ED, heart rate (HR) and the percentage ratio of AUCd to AUCs.

In this embodiment, the first recalibration equation (Eq1) is selected if the augmentation index (AIx) is less than 28 and the ejection duration (ED) is less than 300. The second recalibration equation (Eq2) is selected if the augmentation index (AIx) is less than 28 and the ejection duration (ED) is greater than or equal to 300. The third recalibration equation (Eq3) is selected if the augmentation index (AIx) is greater than or equal to 28 and the heart rate (HR) is less than 60. The fourth recalibration equation (Eq4) is selected if the augmentation index (AIx) is greater than or equal to 28 and the heart rate (HR) is greater than or equal to 60 and the ratio of the area under the curve during diastole ($AUC_d$) divided by the area under the curve during systole ($AUC_s$) is less than 100. The fifth recalibration equation (Eq5) is selected if the augmentation index (AIx) is greater than or equal to 28 and the heart rate (HR) is greater than or equal to 60 and the ratio of the area under the curve during diastole ($AUC_d$) divided by the area under the curve during systole ($AUC_s$) is greater than or equal to 100.

Other examples may use more waveform features with more branches in the decision tree. Also, other algorithms that correlate the waveform features with the appropriate NICSP/NICDP to ICSP/ICDP recalibration equation like support vector machine, linear and nonlinear regression, and neural network can also be used as the selection algorithm.

Those skilled in the art will appreciate that it is most desirable to develop the recalibration and selection algorithms for a specific cuff device and NIBP unit. However, the algorithms developed for use for one cuff device and NIBP unit are likely to improve the accuracy of the system using another cuff device and NIBP unit to the extent different models have similar characteristics.

FIGS. 9 through 12 illustrate a system 200 configured in accordance with another embodiment of the invention. The system 200 in FIG. 9, like the system 100 in FIG. 5, includes a non-invasive blood pressure unit 204 (NIBP unit 204), the same as or similar to a conventional brachial cuff "oscillometric" blood pressure device. Beyond the cuff 202 the NIBP unit 204 includes, e.g., a pressure tube, an air pressure control, and a pressure sensor for sensing the pressure in the cuff 202. As described in connection with the earlier embodiment, the NIBP unit 204 includes control algorithms which operate in the oscillometric mode to determine NISP and NIDP. With a cuff 202 wrapped around the patient's upper arm (including the brachial artery), the NIBP unit 204 performs an oscillometric brachial blood pressure measurement resulting in a value for the non-invasive brachial systolic pressure (NISP) and non-invasive brachial diastolic pressure (NIDP). Then, while the cuff 202 is inflated at a constant pressure (below NIDP, between NIDP and NISP or above NISP for the same reasons described above with respect to the first embodiment), the NIBP unit 204 records a raw cuff waveform 206. As mentioned, previously, it is important that the cuff be inflated with respect to NISP and NIDP consistent with the inflation of the cuff for the data collected to determine the recalibration equations discussed below. As in the earlier embodiment described in connection with FIG. 5, the raw cuff waveform 206 is processed through a high pass filter and low pass filter or a band pass filter, see block 208, to produce a pre-calibrated brachial cuff waveform 210 with cardiovascular related features preserved. This waveform 210 is brachial cuff volumetric displacement waveform, which contains and preserves the cardiovascular features present in the patient's brachial artery pressure waveform, however, the amplitude of the waveform 210 needs to be calibrated. Alternatively, like the embodiment shown in FIG. 5, the pre-calibrated peripheral waveform 210 can be measured non-invasively using a tonometer, photodiode or other pressure sensor. As mentioned, using a pressure sensor to record the pre-calibrated peripheral waveform 210 means that the recalibration equations and transfer function(s) do not need to be customized for the pressure of the inflated cuff when capturing the waveform.

Figure 9:
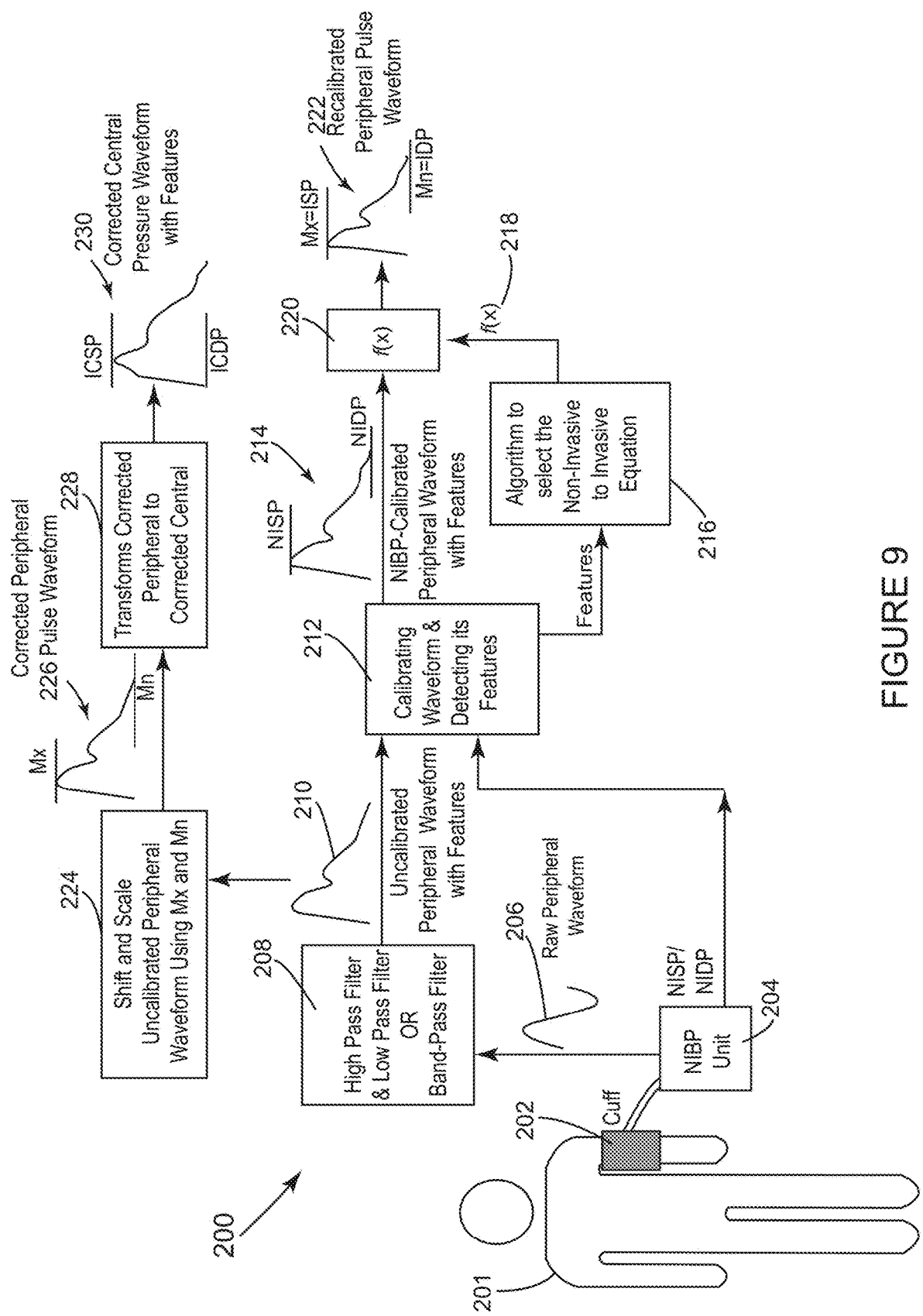
FIG. 9 is the schematic drawing illustrating a second embodiment of the invention, which records a non-invasive brachial waveform, measures NISP and NIDP using a brachial cuff device, estimates brachial ISP and IDP and optionally provides a scaled central aortic pressure waveform in which the maximum and the minimum provide a close estimate to ICSP and ICDP.

The operations after the NIBP unit 204 in FIG. 9 are preferably implemented in a digital signal processor, or other computing device. However, the electronic filters discussed in connection with block 208 can be analog or digital, with analog-to-digital conversion occurring after block 208 or prior to block 208, respectively.

Block 212 in FIG. 9 depicts both the pre-calibrated peripheral waveform 210 (with features preserved) and the NISP and NIDP values being entered into an algorithm (e.g. software code) that calibrates the pre-calibrated peripheral waveform 210 so that the maximum and minimum values of waveform 210 are equivalent to NISP and NIDP, respectively. This NISP/NIDP calibration results in a NIBP-calibrated peripheral waveform 214 with preserved features. In addition, the software depicted in block 212 also determines parameter values for cardiovascular related features of the NIBP-calibrated peripheral waveform 214. The specific cardiovascular features used in this exemplary embodiment are explained in connection with FIG. 11.

Figure 10:
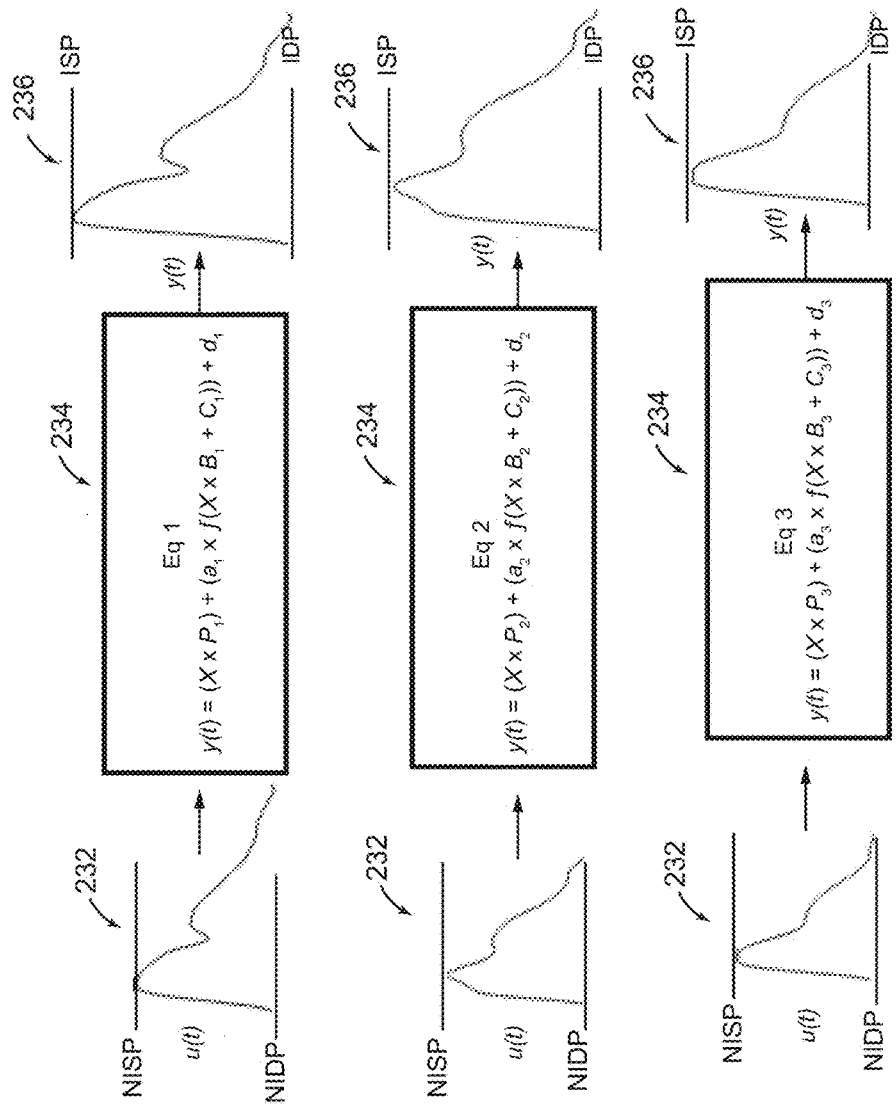
FIG. 10 shows an exemplary form of non-invasive to invasive central blood pressure waveform recalibration equations for NIBP-calibrated brachial cuff waveforms having different waveform shapes.
Figure 12:
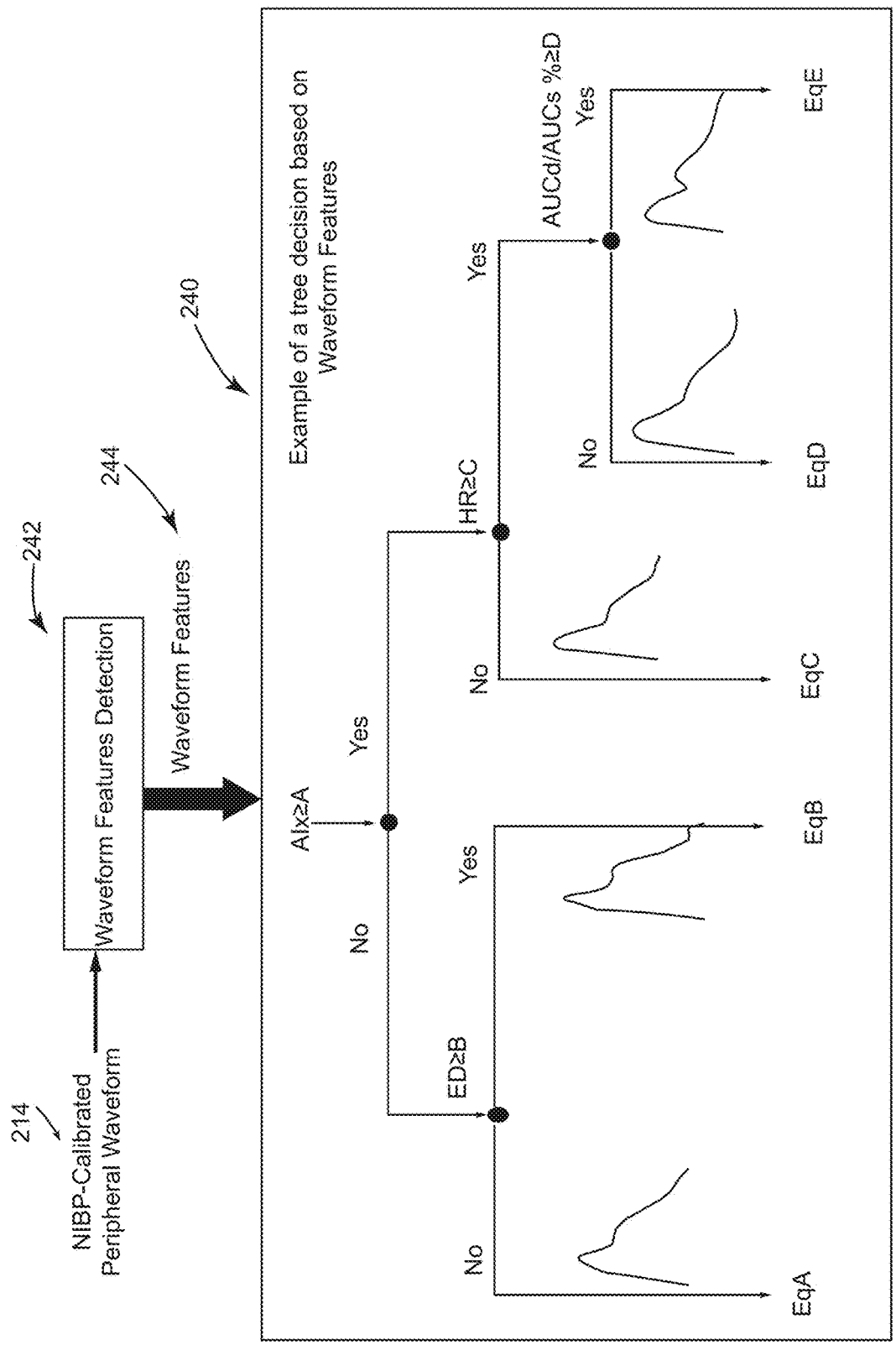
FIG. 12 shows an example decision tree based on cardiovascular features of a NIBP-calibrated brachial cuff waveform that determines which non-invasive to invasive recalibration equation should be used.

Referring still to FIG. 9, the determined feature parameter values from block 212 are the input for a selection algorithm, block 216, that determines which recalibration equation $f_i(x)$, reference number 218, should be used to recalibrate the NIBP-calibrated peripheral waveform 214 in terms of invasive brachial blood pressure instead of non-invasive brachial blood pressure. Examples of a selection algorithm 216 and recalibration equations 218 are shown in FIG. 12 and FIG. 10 respectively, and are discussed in more detail below. Block 220 in FIG. 9 indicates that the selected recalibration equation 218 operates on the NIBP-calibrated peripheral waveform 214, to produce a recalibrated peripheral waveform 222 where the maximum (Mx) and the minimum (Mn) values provide accurate estimates of the invasive brachial systolic pressure (ISP) and invasive brachial diastolic pressure (IDP), respectively.

The non-invasive to invasive blood pressure recalibration equations 218 can be developed using the data collected during the testing described above with respect to the embodiment described in FIGS. 5 through 8; however, in this case data of invasive brachial arterial blood pressure (236 in FIG. 10) along with brachial cuff NIBP measurements are used to calculate the recalibration equations. Referring to FIG. 10, again, a method of system identification is used to establish the coefficients and constants for proposed recalibration equations 234 as shown in FIG. 10. The form of the recalibration equations in FIG. 10 is generally the same as the form shown in FIG. 6, and so are the methods of determining appropriate values for the coefficients and constants, except that the input (232) and output 236 for the proposed equations 234 is different.

Applying the system identification method on invasive data collected for a sampling of the general population in this exemplary embodiment again results in five (5) different recalibration equations 218 (see FIG. 10) that can be implemented on the general population. In other words, the final form of the proposed recalibration equations 234 in FIG. 10 corresponds to the recalibration equations 218 programmed in to the system 200. Like the earlier embodiment, the final form of the proposed recalibration equations 234 is determined for different groupings of input 232 and output 236 waveform data, in which the groupings are also based on waveform feature parameters determined by applying the system identification method. In this embodiment, the selection algorithm 216 is again a decision tree that determines which recalibration equation 218 should be used based on waveform features.

Figure 11:
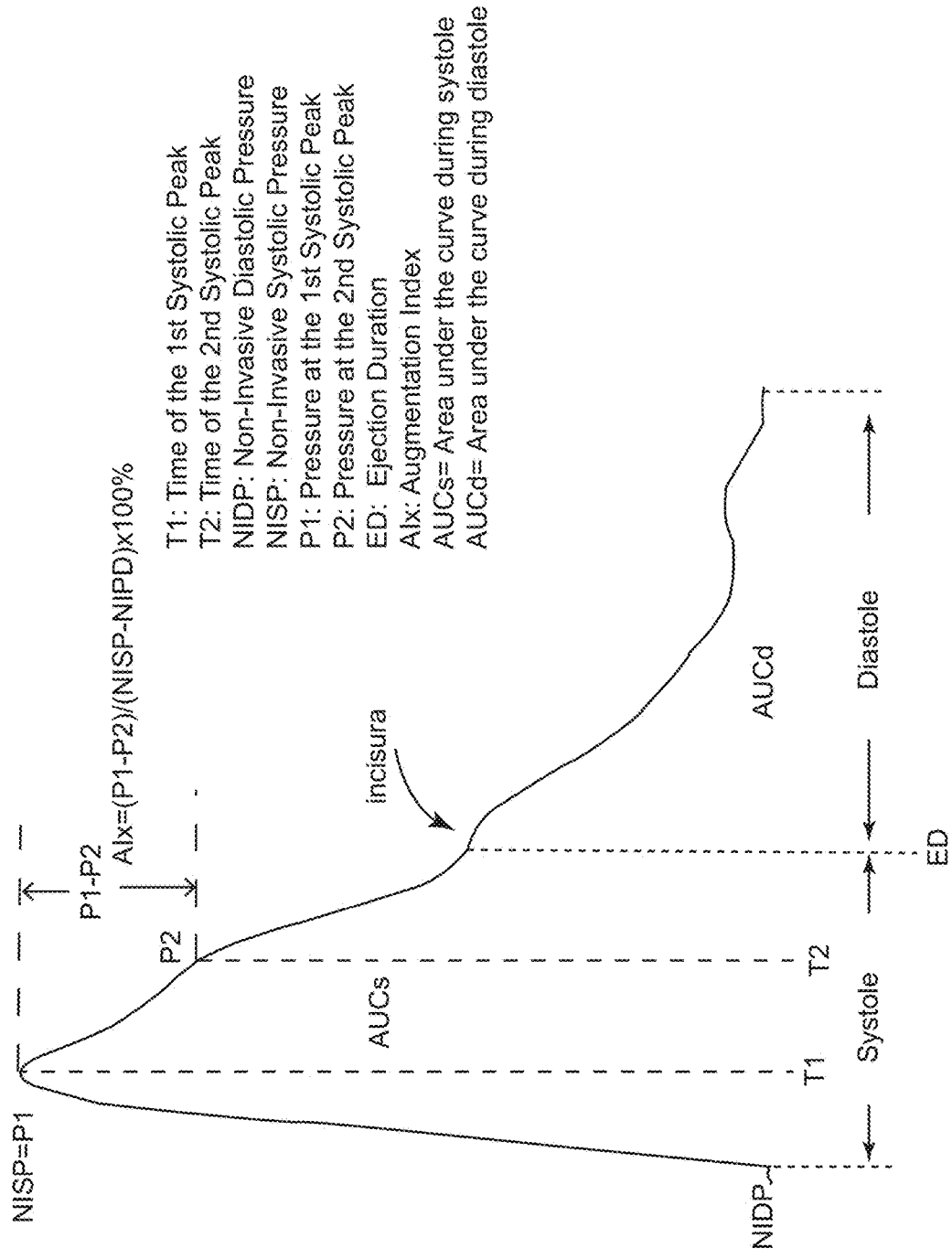
FIG. 11 shows and defines certain cardiovascular features of a NIBP-calibrated brachial cuff waveform.

FIG. 11 describes some of the cardiovascular related features in the NIBP-calibrated peripheral waveform 214 (FIG. 9), which is used as inputs to the selection algorithm 216 in this exemplary embodiment. The features in the embodiment described in FIGS. 9-12 are similar to those described in FIGS. 5-8, however, in FIG. 9 the features pertain to the NIBP-calibrated peripheral waveform 214. These cardiovascular related features and others can be detected or calculated, e.g., using the through derivative method as described in incorporated O'Rourke U.S. Pat. No. 5,265,011, which is hereby incorporated by reference herein, or other suitable mathematical methods in time or frequency like wavelet analysis. Exemplary features that can be used by the selection algorithm include, for example, NISP, NIDP, AIx, AUCs/AUCd, P1, P2, T1, T2, and ED as described in FIG. 11. Other features like mean pressure, heart rate, cardiac period and slope of the systolic upstroke, which also can be detected from the NIBP calibrated waveform, can also be used as input to the algorithm.

FIG. 12 illustrates one exemplary selection algorithm 240 in the form of a decision tree that is used to determine the appropriate recalibration equation (EqA, EqB, EqC, EqD and EqE) based on the detected or calculated waveform features or parameters. Block 242 in FIG. 12 depicts pulse waveform features 244 being detected from the NIBP-calibrated peripheral waveform 214. As mentioned, suitable feature detection methods include the derivative method or other mathematical methods in time or frequency domain. The values detected or calculated pertaining to the waveform features 244 are the input to the decision tree 240, which in this example serves as the selection algorithm 216 in FIG. 9. In FIG. 12, one of five NISP/NIDP to ISP/IDP recalibration equations (EqA, EqB, EqC, EqD or EqE) is selected based on values of AIx, ED, heart rate (HR) and the percentage ratio of AUCd to AUCs.

Referring again to FIG. 9, block 220 indicates that the selected recalibration equation 218 operates on the NIBP-calibrated peripheral waveform 214, to produce a recalibrated waveform 222 where the maximum (Mx) and the minimum (Mn) values provide accurate estimates of the invasive systolic pressure (ISP) and invasive diastolic pressure (IDP) in the brachial artery, respectively. While the waveform 222 provides accurate estimates of ISP and IDP, the shape of the waveform 222 may be unnecessarily distorted compared to the shape of the NIBP-calibrated peripheral waveform 214 and therefore may not be optimal for central pressure waveform analysis in a clinical or research setting. Still referring to FIG. 9, block 224 depicts the software using Mx and Mn from the recalibrated peripheral waveform 222 as input to shift and/or scale the pre-calibrated peripheral waveform 210 (or, alternatively, the NIBP-calibrated peripheral waveform 214), thereby resulting in a corrected peripheral waveform 226. The corrected peripheral waveform 226 accurately embodies the shape and amplitude of the peripheral waveform as if it were measured invasively. This waveform 226 as well as Mx and Mn can be used in clinical and research applications to more accurately depiction the peripheral waveform shape and size. FIG. 9 also shows block 228 illustrating that the corrected peripheral waveform 226 can be used as input for one or more transfer functions to convert the corrected peripheral waveform 226 into a corrected central pressure waveform 230. The transfer method described in above incorporated Qasem patent should be used to convert the corrected peripheral waveform 226 into a corrected central pressure waveform 230. The corrected central pressure waveform 230 accurately embodies the shape and amplitude of the central pressure waveform as if it were measured invasively.

Those skilled in the art will again appreciate that it is most desirable to develop the recalibration and selection algorithms for a specific cuff device and NIBP unit. However, the algorithms developed for use with one cuff device and NIBP unit are likely to improve the accuracy of the detected SP and DP for another cuff device and NIBP unit to the extent different models have similar characteristics.

Results: Referring to the system 100 shown in the first embodiment in FIGS. 5 through 8, using a subset of the collected data to train a decision tree where the inputs are waveform features and the outputs were the recalibration equations (Eq1, Eq2, Eq3, Eq4 and Eq5), the decision tree showed, for example: that if NICDP less than 70, ED larger than or equal to 350, AIx is less than 27, and the percentage ratio of AUCd to AUCs larger than or equal to 140 then Eq1 is chosen as the recalibration equation. If NICDP less than 70, ED larger than or equal to 350 and AIx is larger than 27 then Eq2 is chosen as the recalibration equation. If NICDP greater than or equal to 70, the percentage ratio of AUCd to AUCs is larger than 100, AIx is less than 20, HR less than 60 and ED is less than 390 then Eq3 is chosen as the recalibration equation. If NICDP greater than or equal to 70, the percentage ratio of AUCd to AUCs is larger than 100, AIx is less than 20, HR larger than or equal to 60, and NICDP greater than or equal to 90 then Eq4 is chosen as the recalibration equation. If NICDP greater than or equal to 70, the percentage ratio of AUCd to AUCs is larger than 100, AIx is less than 20, and HR larger than or equal to 60, and NICDP less than 90 then Eq5 is chosen as the recalibration equation.

Figure 13A:
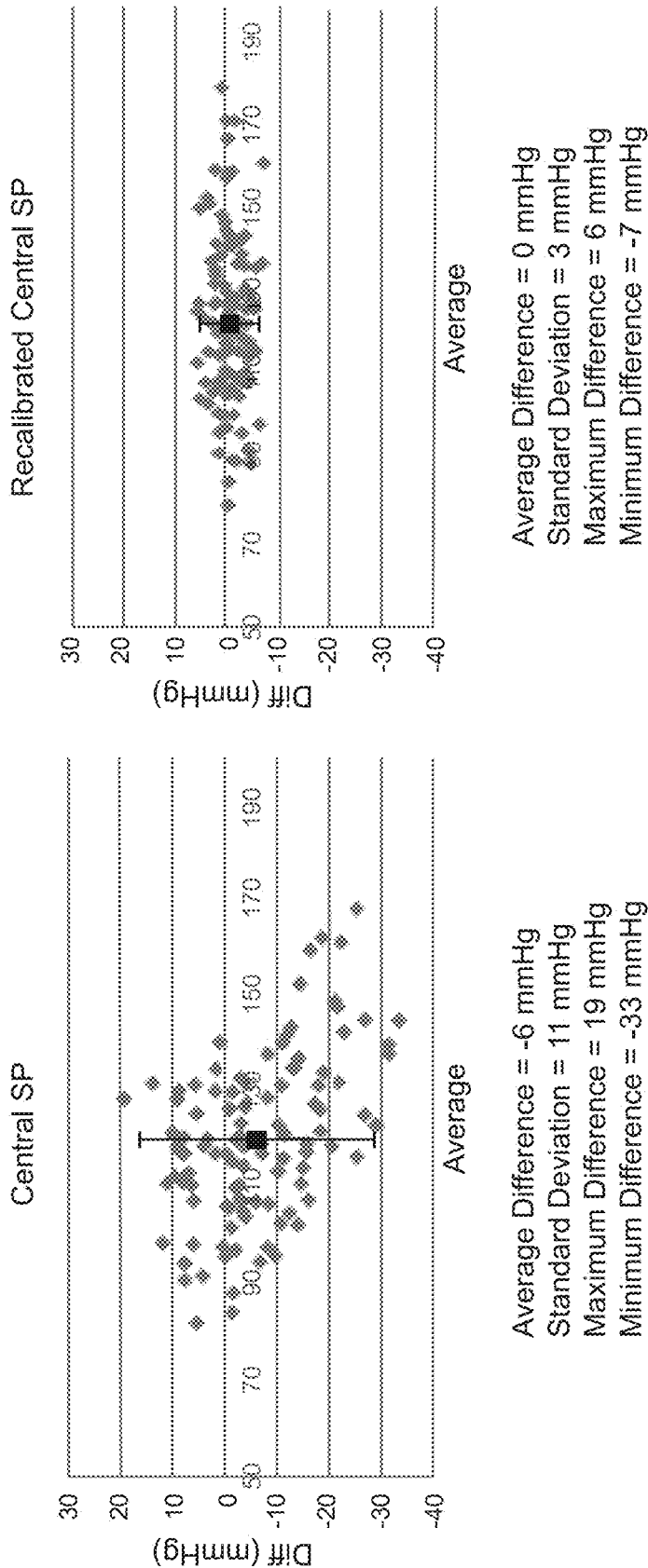
FIG. 13A includes a left side and a right side plot of data. The left side plots the average value of invasive central systolic pressure (SP) versus the difference between NIBP-calibrated non-invasive central SP and invasive central SP. The right side is a plot of the average value of invasive central SP versus the difference between recalibrated, non-invasive central SP and invasive central SP. The left text box shows the average, standard deviation, the maximum and the minimum difference between NIBP-calibrated and invasive central SP. The right text box shows the average, standard deviation, the maximum and the minimum difference between recalibrated, non-invasive and invasive central SP.

When applying the determined decision tree on the tested data (N=110), the results and the plots are shown in FIG. 13. The graph on the left in FIG. 13A shows the plot of the average of versus the difference between NIBP and invasive central systolic pressure (SP). After applying the recalibration equation as determined by the decision tree and based on the waveform features, the graph on the right in FIG. 13A shows large, significant reductions in the difference between the recalibrated and the invasive central SP—illustrating the accuracy of the recalibration. The average and standard deviation of the difference were reduced significantly from −6±11 mmHg to 0±3 mmHg.

Figure 13B:
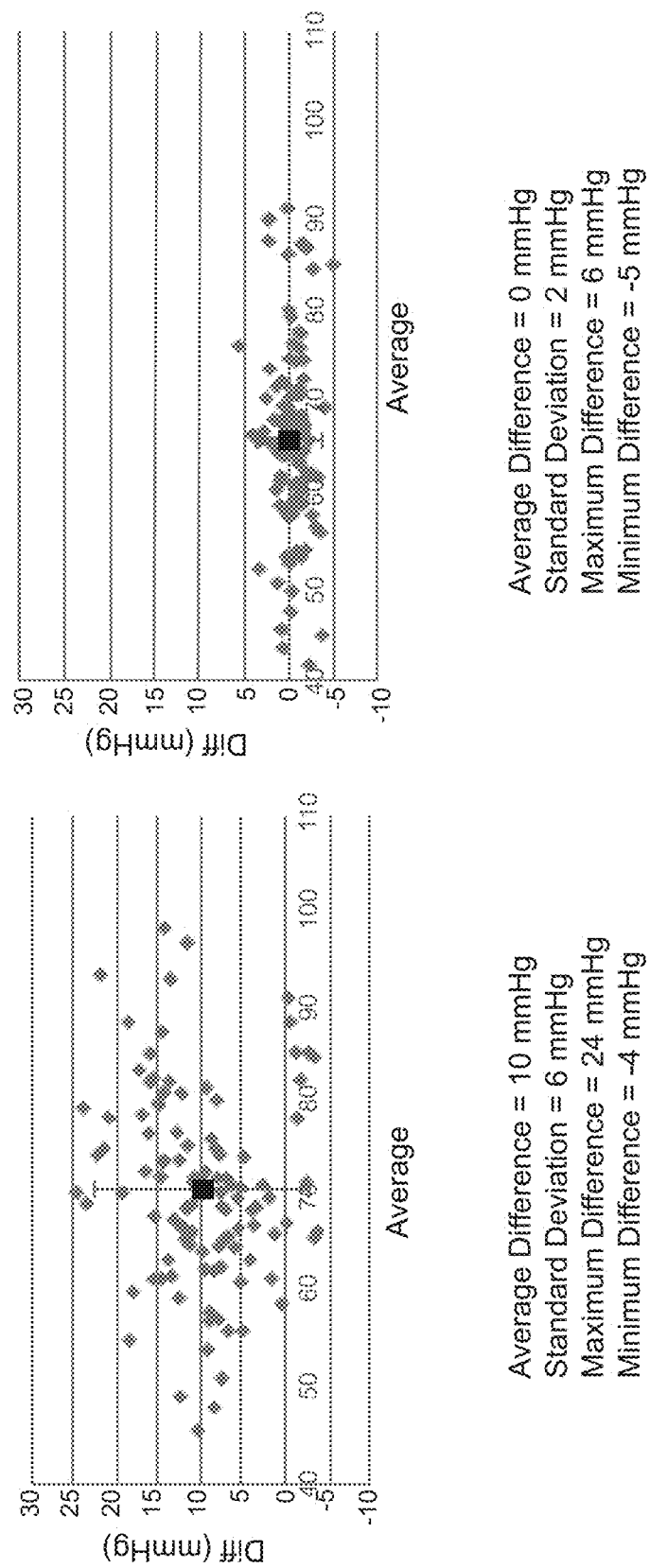
FIG. 13B includes a left side and a right side plot of data. The left side plots the average value of invasive central diastolic pressure (DP) versus the difference between NIBP-calibrated non-invasive central DP and invasive central DP. The right side is a plot of the average value of invasive central DP versus the difference between recalibrated, non-invasive central DP and invasive central DP. The left text box shows the average, standard deviation, the maximum and the minimum difference between NIBP-calibrated and invasive central DP. The right text box shows the average, standard deviation, the maximum and the minimum difference between recalibrated, non-invasive and invasive central DP.

The graph on the left side in FIG. 13B shows the plot of the average value of invasive central diastolic pressure (DP) versus the difference between NIBP-calibrated and invasive central diastolic pressure (DP). After applying the recalibration equation as determined by the decision tree and based on the waveform features, the graph on the right in FIG. 13B shows large, significant reductions in the difference between the recalibrated and the invasive central DP illustrating the accuracy of the recalibration. The average and standard deviation of the difference were reduced significantly from 10±6 mmHg to 0±2 mmHg.

In the foregoing description, certain terms have been used for brevity, clarity, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims. Each limitation in the appended claims is intended to invoke interpretation under 35 U.S.C. § 112, sixth paragraph, only if the terms "means for" or "step for" are explicitly recited in the respective limitation.

The invention claimed is:

1. A blood pressure measuring method, the method comprising the steps:

providing a brachial cuff device having an inflatable cuff and wrapping the inflatable cuff around the upper arm of a patient and measuring the patient's brachial systolic blood pressure ($SP_B$) and brachial diastolic blood pressure ($DP_B$) using the brachial cuff device in oscillometric mode;

using a non-invasive sensor to record an uncalibrated pulse waveform for a peripheral artery of the patient, wherein the fidelity of the recorded, uncalibrated peripheral waveform is sufficient to preserve the cardiovascular features of the waveform;

using at least two from a group consisting of the brachial systolic pressure ($SP_B$), brachial mean pressure ($MP_B$) and brachial diastolic pressure ($DP_B$) to NIBP-calibrate the recorded, uncalibrated peripheral waveform, wherein the brachial mean pressure ($MP_B$), if used, is determined from the measured brachial systolic pressure ($SP_B$) and the measured brachial diastolic pressure ($DP_B$);

converting the NIBP-calibrated peripheral pulse waveform having its cardiovascular waveform features preserved to a NIBP-calibrated central pressure waveform having its cardiovascular waveform features preserved;

recalibrating the NIBP-calibrated central aortic pressure waveform based on one or more cardiovascular features in the NIBP-calibrated central pressure waveform so that the maximum and minimum of the recalibrated central pressure waveform correspond with invasive central systolic pressure (ICSP) and invasive central diastolic pressure (ICDP) respectively.

2. The method as recited in claim 1 wherein the step of converting the NIBP-calibrated peripheral pulse waveform to the NIBP-calibrated central pressure waveform comprises a use of one or more generalized transfer functions that represent the harmonic ratio in amplitude and phase to transform the NIBP-calibrated peripheral pulse waveform having cardiovascular waveform features preserved to an estimated central pressure waveform having its cardiovascular features preserved.

3. The method as recited in claim 1 wherein the recalibrating step further comprises the steps of:

determining one or more parameter values pertaining to the cardiovascular features of the NIBP-calibrated central pressure waveform;

providing multiple recalibration equations;

and selecting one of the multiple recalibration equations based on the determined values for the one or more parameters pertaining to the cardiovascular features of the NIBP-calibrated central pressure waveform.

4. The method as recited in claim 1 wherein the uncalibrated, peripheral pulse waveform is a radial pressure waveform measured using a tonometer or a photodiode sensor.

5. The method as recited in claim 1 wherein the uncalibrated peripheral pulse waveform is a brachial volumetric displacement waveform measured by inflating the brachial cuff around a patient's upper arm to a constant pressure and recording the patient's brachial cuff volumetric waveform using a digital signal processor to generate filtered data that preserves the cardiovascular waveform features of the patient's brachial cuff volumetric displacement waveform.

6. The method as recited in claim 5 wherein the NIBP-calibrated peripheral pulse waveform is a NIBP-calibrated brachial volumetric displacement waveform and the step of converting the NIBP-calibrated brachial volumetric displacement waveform to the NIBP-calibrated central pressure waveform comprises a use of one or more generalized transfer functions represent the harmonic ratio in amplitude and phase to transform the NIBP-calibrated brachial cuff volumetric displacement waveform having cardiovascular waveform features preserved to the estimated aortic pressure waveform having cardiovascular waveform feature preserved when the brachial cuff is inflated to said constant pressure.

7. The method as recited in claim 3 wherein the selected recalibration equation is selected based on a decision tree which considers the patient's augmentation index (AIx), ejection duration (ED), heartrate (HR) and the percentage ratio of the area under the curve during diastole over the area under the curve during systole (AUCd/AUCs).

8. The method as recited in claim 3 wherein the multiple recalibration equations have a common form with linear and nonlinear components but coefficients and scaler constants that account for differences between invasive blood pressure measurements and non-invasive blood pressure measurements for the given combination of cardiovascular parameter values over the general population.

9. The invention as recited in claim 2 wherein the multiple recalibration equations are determined by comparing data collected from a sampling of a general population, said data comprising at least waveform data measuring with a brachial cuff inflated to a constant pressure, brachial systolic and diastolic blood pressure values measured using a brachial cuff in oscillometric mode, and invasively measured central systolic and diastolic blood pressure.

10. The method as recited in claim 2 wherein the multiple recalibration equations include linear components and non-linear components.

11. The method as recited in claim 10 wherein each of the multiple recalibration equations as the following form:

$$y(t) = ([u(t)\ u(t-1)\ \ldots\ u(t-na)\ y(t-1)\ \ldots\ y(t-nb)] \times P_i) +$$
$$(a_i \times f([u(t)\ u(t-1)\ \ldots\ u(t-na)\ y(t-1)\ \ldots\ y(t-nb)] \times B_i + C_i))$$

where
$y(t)$ is the output waveform at time t
$P_i$, is na+nb+1 by 1 matrix of coefficients for recalibration equation i
$B_i$, is na+nb+1 by na+nb+1 square matrix of coefficients for recalibration equation i
$C_i$ is 1 by na+nb+1 matrix of coefficients for recalibration equation i
na, nb are the number of delay points for the input and output signals respectively,
$a_i$, $d_i$ are scalars (constants) for recalibration equation i
$u(t)$ is the input waveform at time t,
$u(t-1)$ is the input waveform at time t−1,
$u(t-na)$ is the input waveform at time t—na,
$y(t-1)$ is the output waveform at time t−1,
$y(t-nb)$ is the input waveform at time t−nb, and
and f( ) is a non-linear sigmoid function expressed as follows:

$$f(z) = \frac{1}{e^{-z}+1}.$$

12. The method as recited in claim 8 wherein a first recalibration equation is selected if the augmentation index (AIx) is greater than or equal to an AIx threshold value and the ejection duration (ED) is greater than or equal to an ED threshold value, a second recalibration equation is selected if the augmentation index (AIx) is greater than or equal to an AIx threshold value and the ejection duration (ED) is less than an ED threshold value, a third recalibration equation is selected if the augmentation index (AIx) is less than an AIx threshold value and the heart rate (HR) is greater or equal to an HR threshold value, a fourth recalibration equation is selected if the augmentation index (AIx) is less than an AIx threshold value and the heart rate (HR) is less than an HR threshold value and the ratio of the area under the curve during diastole ($AUC_d$) divided by the area under the curve during systole ($AUC_s$) is greater than or equal to an AUC threshold value, and, a fifth recalibration equation is selected if the augmentation index (AIx) is less than an AIx threshold value and the heart rate (HR) is less than an HR threshold value and the ratio of the area under the curve during diastole ($AUC_d$) divided by the area under the curve during systole ($AUC_s$) is less than an AUC threshold value.

13. The method as recited in claim 1 further comprising the step of generating a corrected central pressure waveform with its cardiovascular features preserved by shifting and scaling the NIBP-calibrated central pressure waveform to result in the corrected central pressure waveform, wherein the maximum and minimum of the corrected central pressure waveform are set equal to the maximum and minimum of the recalibrated central pressure waveform respectively.

14. The method recited in claim 2 wherein the one or more generalized transfer functions includes a generalized transfer function that transforms the NIBP-calibrated peripheral pulse waveform directly to the NIBP-calibrated central pressure waveform, said transfer function being based on peripheral and central pulse waveform data collected invasively on a sample representing the general population.

15. The method recited in claim 2 wherein one or more generalized transfer functions comprise at least:
a first generalized transfer function that mathematically transforms the NIBP-calibrated peripheral pulse waveform to an intermediate artery pressure waveform and a second generalized transfer function that transforms the intermediate artery pressure waveform to the NIBP-calibrated central pressure waveform, said second transfer function being based on peripheral and central pulse waveform data collected invasively on a sample representing the general population.

16. The method recited in claim 5 wherein the brachial cuff is inflated around the patient's upper arm to a constant pressure that is defined by the following equation $$P_{Cuff} = K\%*DP_B$$

where K % ranges from 10 to 90%.

17. The method recited in claim 5 wherein the brachial cuff is inflated around the patient's upper arm to a constant pressure that is defined by the following equation $$P_{Cuff} = (K\%)(SP_B - DP_B) + DP_B$$

where K % is chosen to be between 10% and 90%.

18. The method recited in claim 5 wherein the brachial cuff is inflated around the patient's upper arm to a constant pressure that is defined by the following equation $$P_{Cuff} = [(K\%) + 1]SP_B$$

where K % ranges from 10 to 90%.

19. The method recited in claim 3 wherein the recalibration equations are determined from simultaneously recorded invasive and non-invasive data for a general population, and NIBP-calibrated central pressure waveform data is compared to invasively measured central pressure waveform data in order to determine the recalibration equations.

20. The method as recited in claim 1 wherein the NIBP-calibrated peripheral pulse waveform that is converted using one or more generalized transfer functions to the NIBP-calibrated central pressure waveform with its cardiovascular waveform features preserved comprises an average of multiple recorded and NIBP-calibrated peripheral pulse waveforms measured by the sensor.

21. The method as recited in claim 5 wherein the brachial cuff is part of a device that comprises the brachial cuff, a tube, a pressure pump with a pressure control system, and a pressure sensor that provides an analog signal and the blood pressure measuring system further comprises the digital signal processor that has a low pass filter and a high pass filter, receives the analog signal from the pressure sensor and outputs a digital brachial cuff signal containing filtered data preserving the cardiovascular waveform features of patient's brachial cuff volumetric displacement waveform, and a computer that receives the digital brachial cuff signal, records and NIBP-calibrates the brachial cuff waveform, and converts the NIBP-calibrated brachial cuff waveform to the NIBP-calibrated central pressure waveform having cardiovascular waveform features preserved using one or more transfer functions calculated for use when the brachial cuff is inflated to a pressure within the selected pressure range comprising one of below $DP_B$, above $SP_B$ or between $DP_B$ and $SP_B$.

22. The method recited in claim 13 further comprising the step of displaying the corrected central pressure waveform as a trace or otherwise on a computer display screen.

23. A blood pressure measuring method, the method comprising the steps:
providing a brachial cuff device having an inflatable cuff and wrapping the inflatable cuff around the upper arm of a patient and measuring the patient's brachial systolic blood pressure ($SP_B$) and brachial diastolic blood pressure ($DP_B$) using the brachial cuff device in oscillometric mode;
using a non-invasive sensor to record an uncalibrated pulse waveform for a peripheral artery of the patient, wherein the fidelity of the recorded, uncalibrated peripheral waveform is sufficient to preserve the cardiovascular features of the waveform;
using at least two from a group consisting of the brachial systolic pressure ($SP_B$), brachial mean pressure ($MP_B$) and brachial diastolic pressure ($DP_B$) to NIBP-calibrate the recorded, uncalibrated peripheral waveform, wherein the brachial mean pressure ($MP_B$), if used, is determined from the measured brachial systolic pressure ($SP_B$) and the measured brachial diastolic pressure ($DP_B$);
recalibrating the NIBP-calibrated peripheral pulse waveform based on one or more cardiovascular features in the NIBP-calibrated peripheral pulse waveform so that the maximum and minimum of the recalibrated peripheral pulse waveform correspond with invasive peripheral systolic pressure (ISP) and invasive peripheral diastolic pressure (IDP) respectively;
generating a corrected peripheral pulse waveform with its cardiovascular features preserved by shifting and scaling the uncalibrated peripheral pulse waveform to result in the corrected peripheral pulse waveform such that the maximum and minimum of the corrected peripheral pulse waveform are set equal to the maximum and minimum of the recalibrated peripheral pulse waveform; and
converting the corrected peripheral pulse waveform having its cardiovascular waveform features preserved to a corrected central pressure waveform having its cardiovascular waveform features preserved.

24. The method as recited in claim 23 wherein a maximum and minimum of the corrected central pressure waveform correspond with invasive central systolic pressure (ICSP) and invasive central diastolic pressure (ICDP), respectively.

25. The method as recited in claim 23 further comprising the step of displaying the corrected central pressure waveform as a trace or otherwise on a computer display screen.

26. The method as recited in claim 23 wherein the step of converting the corrected peripheral pulse waveform to the corrected central pressure waveform comprises the use of one or more generalized transfer functions that represent the harmonic ratio in amplitude and phase to transform a calibrated peripheral pulse waveform having cardiovascular waveform features preserved to an estimated central pressure waveform having its cardiovascular features preserved.

27. The method as recited in claim 23 wherein the recalibrating step further comprises the steps of:
determining one or more parameter values pertaining to the cardiovascular features of the NIBP-calibrated peripheral pulse waveform;
providing multiple recalibration equations;
and selecting one of the multiple recalibration equations based on the determined values for the one or more parameters pertaining to the cardiovascular features of the NIBP-calibrated peripheral pulse waveform.

28. The method as recited in claim 23 wherein the uncalibrated peripheral pulse waveform is a radial pressure waveform measured using a tonometer or a photodiode sensor.

29. The method as recited in claim 23 wherein the uncalibrated peripheral pulse waveform is a brachial volumetric displacement waveform measured by inflating the brachial cuff around a patient's upper arm to a constant pressure and recording the patient's brachial cuff volumetric waveform using a digital signal processor to generate filtered data that preserves the cardiovascular waveform features of the patient's brachial cuff volumetric displacement waveform.

30. The method as recited in claim 29 wherein the converting step involves the use of one or more generalized transfer functions represent the harmonic ratio in amplitude and phase to transform a calibrated brachial cuff volumetric displacement waveform having cardiovascular waveform features preserved to an estimated aortic pressure waveform having cardiovascular waveform feature preserved when the brachial cuff is inflated to said constant pressure.

31. The method as recited in claim 27 wherein the appropriate recalibration equation is selected based on a decision tree which considers the patient's augmentation index (AIx), ejection duration (ED), heartrate (HR) and the percentage ratio of the area under the curve during diastole over the area under the curve during systole (AUCd/AUCs).

32. The method as recited in claim 27 wherein the multiple recalibration equations have a common form with linear and nonlinear components but coefficients and scaler constants being selected to account for differences between invasive blood pressure measurements and non-invasive blood pressure measurements for the given combination of cardiovascular parameter values over the general population.

33. The invention as recited in claim 27 wherein the multiple recalibration equations are determined by comparing data collected from a sampling of a general population, said data comprising at least, peripheral pulse waveform data measured noninvasively, brachial systolic and diastolic blood pressure values measured using a brachial cuff in oscillometric mode, and invasively measured peripheral systolic and diastolic blood pressure.

34. The method as recited in claim 27 wherein the multiple recalibration equations include linear components and non-linear components.

35. The method as recited in claim 34 wherein each of the multiple recalibration equations as the following form:

$$y(t) = ([u(t)\ u(t-1)\ ...\ u(t-na)\ y(t-1)\ ...\ y(t-nb)] \times P_i) + (a_i \times f([u(t)\ u(t-1)\ ...\ u(t-na)\ y(t-1)\ ...\ y(t-nb)] \times B_i + C_i))$$

where
y(t) is the output waveform at time t
$P_i$, is na+nb+1 by 1 matrix of coefficients for recalibration equation i
$B_i$, is na+nb+1 by na+nb+1 square matrix of coefficients for recalibration equation i $C_i$ is 1 by na+nb+1 matrix of coefficients for recalibration equation i na, nb are the number of delay points for the input and output signals respectively, $a_i$, $d_i$ are scalars (constants) for recalibration equation i u(t) is the input waveform at time t, u(t−1) is the input waveform at time t−1, u(t−na) is the input waveform at time t−na, y(t−1) is the output waveform at time t−1, y(t−nb) is the input waveform at time t−nb, and and f( ) is a non-linear sigmoid function expressed as follows:

$$f(z) = \frac{1}{e^{-z}+1}.$$

36. The method as recited in claim 31 wherein a first recalibration equation is selected if the augmentation index (AIx) is greater than or equal to an AIx threshold value and the ejection duration (ED) is greater than or equal to an ED threshold value, a second recalibration equation is selected if the augmentation index (AIx) is greater than or equal to an AIx threshold value and the ejection duration (ED) is less than an ED threshold value, a third recalibration equation is selected if the augmentation index (AIx) is less than an AIx threshold value and the heart rate (HR) is greater or equal to an HR threshold value, a fourth recalibration equation is selected if the augmentation index (AIx) is less than an AIx threshold value and the heart rate (HR) is less than an HR threshold value and the ratio of the area under the curve during diastole ($AUC_d$) divided by the area under the curve during systole ($AUC_s$) is greater than or equal to an AUC threshold value, and, a fifth recalibration equation is selected if the augmentation index (AIx) is less than an AIx threshold value and the heart rate (HR) is less than an HR threshold value and the ratio of the area under the curve during diastole ($AUC_d$) divided by the area under the curve during systole ($AUC_s$) is less than an AUC threshold value.

37. The method recited in claim 26 wherein the one or more generalized transfer functions includes a generalized transfer function is based on peripheral and central pulse waveform data collected invasively on a sample representing the general population.

38. The method recited in claim 26 wherein one or more generalized transfer functions comprise at least:

a first generalized transfer function that mathematically transforms the corrected peripheral pulse waveform to an intermediate artery pressure waveform and a second generalized transfer function that transforms the intermediate artery pressure waveform to the corrected central pressure waveform, said second transfer function being based on peripheral and central pulse waveform data collected invasively on a sample representing the general population.

39. The method recited in claim 29 wherein the brachial cuff is inflated around the patient's upper arm to a constant pressure that is defined by the following equation $P_{Cuff} = K\% * DP_B$ where K % ranges from 10 to 90%.

40. The method recited in claim 29 wherein the brachial cuff is inflated around the patient's upper arm to a constant pressure that is defined by the following equation $P_{Cuff} = (K\%)(SP_B - DP_B) + DP_B$ where K % is chosen to be between 10% and 90%.

41. The method recited in claim 29 wherein the brachial cuff is inflated around the patient's upper arm to a constant pressure that is defined by the following equation $P_{Cuff} = [(K\%)+1]SP_B$ where K % ranges from 10 to 90%.

42. The method recited in claim 27 wherein the recalibration equations are determined from simultaneously recorded invasive and non-invasive data for a general population, and NIBP-calibrated peripheral pulse waveform data is compared to invasively measured peripheral pulse waveform data in order to determine the recalibration equations.

43. The method as recited in claim 26 wherein the corrected peripheral pulse waveform that is converted using one or more generalized transfer functions to the corrected central pressure waveform with its cardiovascular waveform features preserved comprises an average of multiple recorded and corrected peripheral pulse waveforms measured by the sensor.

44. The method as recited in claim 29 wherein the brachial cuff is part of a device that comprises the brachial cuff, a tube, a pressure pump with a pressure control system, and a pressure sensor that provides an analog signal and the blood pressure measuring system further comprises the digital signal processor that has a low pass filter and a high pass filter, receives the analog signal from the pressure sensor and outputs a digital brachial cuff signal containing filtered data preserving the cardiovascular waveform features of patient's brachial cuff volumetric displacement waveform, and a computer that receives the digital brachial cuff signal, records and shifts and scales the brachial cuff waveform to generate a corrected brachial cuff waveform, and converts the corrected brachial cuff waveform to the corrected central pressure waveform having cardiovascular waveform features preserved using one or more transfer functions calculated for use when the brachial cuff is inflated to a pressure within the selected pressure range comprising one of below $DP_B$, above $SP_B$ or between $DP_B$ and $SP_B$.

* * * * *